US011046994B2

(12) United States Patent
Zhao et al.

(10) Patent No.: US 11,046,994 B2
(45) Date of Patent: Jun. 29, 2021

(54) METHOD FOR ASSESSING JUICE/CIDER QUALITY AND/OR SAFETY

(71) Applicant: The United States of America, as represented by the Secretary of Agriculture, Washington, DC (US)

(72) Inventors: Wei Zhao, Port St. Lucie, FL (US); Elizabeth A Baldwin, Winter Haven, FL (US); Jinhe Bai, Port St. Lucie, FL (US); Anne Plotto, Winter Haven, FL (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 288 days.

(21) Appl. No.: 16/027,686

(22) Filed: Jul. 5, 2018

(65) Prior Publication Data

US 2018/0305741 A1 Oct. 25, 2018

Related U.S. Application Data

(62) Division of application No. 14/499,508, filed on Sep. 29, 2014, now Pat. No. 10,047,389.

(60) Provisional application No. 61/884,354, filed on Sep. 30, 2013.

(51) Int. Cl.
*C12Q 1/68* (2018.01)
*C12Q 1/6806* (2018.01)
*C12Q 1/689* (2018.01)
*C12Q 1/6888* (2018.01)

(52) U.S. Cl.
CPC .......... *C12Q 1/6806* (2013.01); *C12Q 1/689* (2013.01); *C12Q 1/6888* (2013.01)

(58) Field of Classification Search
CPC ..... C12Q 1/6806; C12Q 1/6888; C12Q 1/689
See application file for complete search history.

(56) References Cited

PUBLICATIONS

Alaey, Mitta et al., "Comparing Study Between Four Different Methods of Genomic DNA Extraction from Cyclamen persicum Mill", (2005) International Journal of Agriculture & Biology, 7(6):882-884.
Allen, GC et al., "A modified protocol for rapid DNA isolation from plant tissues using cetyltrimethylammonium bromide", (2006) Nature Protocols, 1(5):2320-2325.
Arias, Covadonga R. et al., "Yeast Species Associated with Orange Juice: Evaluation of Different Identification Methods", (2012) Applied and Environmental Microbiology, 68(4):1955-1961.
Bai, Jinhe et al., "Detection of 16S rDNA of Candidatus Liberibacter asiaticus in Orange Juice by Quantitative Real-time PCR", (2012) Proceedings Florida State Horticultural Society 125:233-238.
Baldwin, Elizabeth et al., "Effect of Liberibacter Infection (Huanglongbing Disease) of Citrus on Orange Fruit Physiology and Fruit/Fruit Juice Quality: Chemical and Physical Analyses", (2010) Journal of Agricultural and Food chemistry 58:1247-1262.
Dellaporta, Stephen I., Jonathan Wood and James B. Hicks, "A Plant DNA Minipreparation: Version II", (1983) Plant Molecular Biology Reporter 1(4):19-21.
Deng, Ming Qi and Dean O. Cliver, "Comparative detection of Cryptosporidium parvum oocysts from apple juice", (2000) International Journal of Food Microbilology 54:155-162.
Morgan, J. Kent et al., "Improved real-time PCR detection of 'Candidatus Liberibacter asiaticus' from citrus and psyllid hosts by targeting the intragenic tandem-repeats of its prophage genes", (2012) Molecular and Cellular Probes 26:90-98.
Gonzalez-Mendoza, D. et al., "A rapid method for isolation of total DNA from pathogenic filamentous plant fungi", (2010) Genetics and Molecular Research 9(1):162-166.
Gottwald, T.R. et al., "Inconsequential effect of nutritional treatments on huanglongbing control, fruit quality, bacterial titer and disease progress", (2012) Crop Protection 36:73-82.
Han, Jianxun et al., "PCR and DHPLC methods used to detect juice ingredient from 7 fruits", (2012) Food control 25:696-703.
Justesen, Ulla, Pia Knuthsen and Torben Leth, "Quantitative analysis of flavonols, flavones, and flavanones in fruits, vegetables and beverages by high-performance liquid chromatography with photo-diode array and mass spectrometric detection", (1998) Journal of Chromatography A 799:101-110.
Kim, Hye-Jin and Jae-Chang Cho, "Simple and rapid detection of Listeria monocytogenes in fruit juice by real-time PCR without enrichment culture", (2010) Food Control 21:1419-1423.
Li, Wenbin, John S. Hartung and Laurene Levy, "Quantitative real-time PCR for detection and identification of Candidatus Liberibacter species associated with citrus huanglongbing", (2006) Journal of Microbiological Methods 66:104-115.
Li, Wenbin et al., "Optimized Quantification of Unculturable *Candidatus liberibacter* Spp. in Host Plants Using Real-Time PCR", (2008) Plant Disease vol. 92(6):854-861.
Liao, Hui-Ling and Jacqueline K Burns, "Gene expression in Citrus sinensis fruit tissues harvested from huanglongbing-infected trees: comparison with girdled fruit", (2012) Journal of Experimental Botany 63(8): 3307-3319.
Liu, Yin et al., "Real time PCR using TaqMan and SYBR Green for detection of Enterobacter sakazakii in infant formula", (2006) Journal of Microbiological Methods 65:21-31.

(Continued)

*Primary Examiner* — Jezia Riley
(74) *Attorney, Agent, or Firm* — John Fado; Ariel Atkinson

(57) ABSTRACT

A novel method for isolating DNA from juices and ciders is described. This method is low cost and yield large quantities of highly purified DNA even though one uses a small quantity of juice or cider. A method for determining if a juice or cider is safe to consume and/or the quality of the juice or cider are also described. For these methods, one can perform qPCR on the DNA which can be obtained using the disclosed method or any other prior art method, and comparing the amount of DNA from microorganisms is present in the juice and/or cider to determine the safety and/or quality of the juice and/or cider. These methods work even if the liquid was pasteurized.

7 Claims, 6 Drawing Sheets

Specification includes a Sequence Listing.

(56) References Cited

PUBLICATIONS

Mackay, Ian M., Katherine E. Arden and Andreas Nitsche, "Survey and Summary Real-time PCR in virology", (2002) Nucleic Acids Research 30(6):1292-1305.

Noor Adila, A.K. et al., "Comparison of methods for isolating high quality DNA and RNA from an oleaginous fungus Cunninghamella bainieri strain 2a1", (2007) Malaysian Journal of Microbiology 3(1):7-13.

Ogunjimi, Abiodun A. and Prabhakara V. Choudary, "Adsorption of endogenous polyphenols relieves the inhibition by fruit juices and fresh produce of immuno-PCR detection of *Escherichia coli* 0157:H7", (1999) FEMS Immunology and Medical Microbiology 23:213-220.

Okada, Miki, Richard Whitkus and Timothy K Lowrey, "Genetics of Adaptive Radiation in Hawaiian and Cook Islands Species of Tetramolopium (Asteraceae; Astereae). I. Nuclear RFLP Marker Diversity", (1997) American Journal of Botany 84(9):1236-1246.

Pettipher, G.L., M.E. Osmundson and J.M. Murphy, "Methods for the detection and enumeration of Alicyclobacillus acidoterrestris and investigation of growth and production of taint in fruit juice and fruit juice-containing drinks", (1997) Letters in Applied Microbiology 24:185-189.

Plotto, Anne et al., "Effect of Liberibacter Infection (Huanglongbing or "Greening" Disease) of Citrus on Orange Juice Flavor Quality by Sensory Evaluation", (2010) Journal of Food Science 75(4):S220-S230.

Rether, Benoit, Genevieve Delmas and Abdelkrim Laouedj, "Isolation of Polysaccharide-Free DNA from Plants" (1993) Plant Molecular Biology Reporter 11(4):333-337.

Rogstad, Steven H. et al., "DNA Extraction From Plants: The Use of Pectinase", (2001) Plant Molecular Biology Reporter 19:353-359.

Al-Samarrai, T.H. and J. Schmid, "A simple method for extraction of fungal genomic DNA", (2000) Letters in Applied Microbiology 30:53-56.

Saunders, Ginny C., "DNA Extraction", (1999) In: Analytical Molecular Biology: Quality and Validation Chapter 3, pp. 29-46, Cambridge: Published for Laboratory of the Government Chemist by the Royal Society of Chemistry, Teddington, UK.

Scott, Mary and Angus Knight, "Quantitative PCR Analysis for Fruit Juice Authentication Using PCR and Laboratory-on-a-Chip Capillary Electrophoresis According to the Hardy-Weinberg Law", (2009) Journal of Agricultural and Food Chemistry 57:4545-4551.

Scott, Kirsten and Julia Playford, "DNA Extraction Technique for PCR in Rain Forest Plant Species", (1996) BioTechniques 20(6):974-976.

Sheperd, Lara D. and Todd G.B. McLay, "Two micro-scale protocols for the isolation of DNA from polysaccharide-rich plant tissue", (2011) Journal of Plant Research 124:311-314.

Stover, Ed and Greg McCollum, "Incidence and Severity of Huanglongbing and Candidatus Liberibacter asiaticus Titer among Field-infected Citrus Cultivars", (2011) Hoticultural Science 46(10):1344-1348.

Sutherland, John B. et al., "Conversion of Ferulic Acid to 4-Vinylguaiacol by Yeasts Isolated from Frozen Concentrated Orange Juice", (1995) Journal of Food Protection 58(11):1260-1262.

Trivedi, P. et al., "Quantification of viable Candidatus Liberibacter asiaticus in hosts using quantitative PCR with the aid of ethidium monoazide (EMA)", (2009) European Journal of Plant Pathology 124:553-563.

Tsai, Yu-Li and Betty H. Olson, "Rapid method for separation of bacterial DNA from humic substances in sediments for polymerase chain reaction", (1992) Applied and Environmental Microbiology 58(7):2292-2295.

Turechek, W.W. et al., "Evaluation of Quantitative Real-Time PCR Assays for Detection of Citrus Greening", (Jun. 2009) Workshop Proceedings p. 158-160 and Agricultural Research Service Scientific Paper, Publication #241261.

Varma, Astha, Harish Padh and Neeta Shrivastava, "Plant genomic DNA isolation: An art or a science", (2007) Biotechnology Journal 2:386-392.

Wilson, I. G., "Inhibition and Facilitation of Nucleic Acid Amplification", (1997) Applied and Environmental Microbiology 63(10):3741-3751.

Baldwin, Elizabeth et al., "Effect of extraction method on quality of orange juice: hand-squeezed, commercialfresh squeezed and processed", (2012) J. Sci Food Agric 92:2029-2042.

Cai, Rui et al., "Detection of *Alicyclobacillus* spp. in Fruit Juice by Combination of Immunomagnetic Separation and a SYBR Green I Real-Time PCR Assay", (2015) Plos One pp. 1-11, DOI:10.1371/journal.pone.0141049.

Detrana, Nancy Rabalais, "Development of a Real-Time PCR Assay for Detection and Quantification of *Escherichia coli* O157:H7 in Apple Juice", PhD Dissertation, University of Tennessee, (2007).

Duvenage, Wineen, "Detection and Isolation of Thermophilic Acidophilic Bacteria from Fruit Juices" Mater's Thesis, Stellenbosch University, (2006).

Hoehl, Melanie et al., "Low-Cost Bacterial Detection System for Food Safety Based on Automated DNA Extraction, Amplification and Readout", pp. 1302-1304, 17th International Conference on Miniaturized Systems for Chemistry and Life Sciences,Oct. 2013, Freiburg, Germany.

Porebski, Sue et al., "Modification of a CTAB DNA Extraction Protocol for Plants Containing High Polysaccharide and Polyphenol Components", (1997) Plant Molecular Biology Reporter 15(1):8-15.

R-Biopharm AG News, "Juice Analysis with real-time PCR", (2016), 3 pgs., www.r-biopharm.com/news/news-en/juice-analysis-real-time-pcr.

Ros-Chumillas, Maria et al., "Evaluation of a rapid DNA extraction method to detect yeast cells by PCR in orange juice", (2007) Food Control, 8 pgs.

Schrader, C. et al., "PCR inhibitors—occurrence, properties and removal", (2012) Journal of Applied Microbiology 113:1014-1026.

Xiao, Linlin, "Detection of Viable Foodbome Pathogens & Spoilage Microorganisms by Nucleic Acid Amplification Based Platforms", PhD Dissertation, Ohio State University, (2011).

DNA Isolation from Plant: DNeasy Plant Mini Kit—QIAGEN Online Shop. (n.d.). 5 pages, Retrieved Sep. 19, 2017, from qiagen.com/us/shop/sample-technologies/dna/genomic-dna/dneasy-plant-mini-kit/#productdetails.

Bai, Jinhe et al., "Extraction of DNA from Orange Juice, and Detection of Bacterium Candidatus Liberibacter asiaticus by Real-Time PCR", (2013) J. of Agricultural and Food Chemistry 61:9339-9346.

SEQUENCE LISTING

<160> NUMBER OF SEQ ID NOS: 13

<210> SEQ ID NO 1
<211> LENGTH: 27
<212> TYPE: DNA
<213> ORGANISM: Candidatus Liberibacter asiaticus

<400> SEQUENCE: 1
gccgttttaa cacaaaagat gaatatc       27

<210> SEQ ID NO 2
<211> LENGTH: 27
<212> TYPE: DNA
<213> ORGANISM: Candidatus Liberibacter asiaticus

<400> SEQUENCE: 2
ataaatcaat ttgttctagt ttacgac       27

<210> SEQ ID NO 3
<211> LENGTH: 20
<212> TYPE: DNA
<213> ORGANISM: Candidatus Liberibacter asiaticus

<400> SEQUENCE: 3
tcgagcgcgt atgcaatacg       20

<210> SEQ ID NO 4
<211> LENGTH: 24
<212> TYPE: DNA
<213> ORGANISM: Candidatus Liberibacter asiaticus -continued

<400> SEQUENCE: 4
gcgttatccc gtagaaaaag gtag                                          24

<210> SEQ ID NO 5
<211> LENGTH: 18
<212> TYPE: DNA
<213> ORGANISM: Candidatus Liberibacter asiaticus

<400> SEQUENCE: 5
agacgggtga gtaacgcg 18

<210> SEQ ID NO 6
<211> LENGTH: 16
<212> TYPE: DNA
<213> ORGANISM: Alicyclobacillus acidoterrestris

<400> SEQUENCE: 6
atgcagagtt cgaacg 16

<210> SEQ ID NO 7
<211> LENGTH: 17
<212> TYPE: DNA
<213> ORGANISM: Alicyclobacillus acidoterrestris

<400> SEQUENCE: 7
aagctgccga agcactc 17

<210> SEQ ID NO 8
<211> LENGTH: 20
<212> TYPE: DNA
<213> ORGANISM: Saccharomyces spp.

<400> SEQUENCE: 8
gaaaactcca cagtgtgttg 20

<210> SEQ ID NO 9
<211> LENGTH: 19
<212> TYPE: DNA
<213> ORGANISM: Saccharomyces spp.

<400> SEQUENCE: 9
gcttaagtgc gcggtcttg 19

<210> SEQ ID NO 10
<211> LENGTH: 22
<212> TYPE: DNA
<213> ORGANISM: Aspergillus spp.

<400> SEQUENCE: 10
cttggatttg ctgaagacta ac 22

<210> SEQ ID NO 11
<211> LENGTH: 24
<212> TYPE: DNA
<213> ORGANISM: Aspergillus spp.

<400> SEQUENCE: 11
ctaactttcg ttccctgatt aatg 24

<210> SEQ ID NO 12
<211> LENGTH: 21
<212> TYPE: DNA

```
<213> ORGANISM: Escherichia coli

<400> SEQUENCE: 12
atggaatttc gccgattttg c                                          21

<210> SEQ ID NO 13
<211> LENGTH: 20
<212> TYPE: DNA
<213> ORGANISM: Escherichia coli

<400> SEQUENCE: 13
attgtttgcc tccctgctgc                                            20
```

METHOD FOR ASSESSING JUICE/CIDER QUALITY AND/OR SAFETY

CROSS REFERENCE TO RELATED PATENT APPLICATIONS

This patent application claims priority to U.S. patent application Ser. No. 14/499,508 filed on Sep. 29, 2014 (allowed) which claims benefit of U.S. Patent Application 61/884,354 filed Sep. 30, 2013, contents of both of which are expressly incorporated by reference herein.

BACKGROUND OF THE INVENTION

Field of Invention

This invention relates to a novel method for assessing the flavor quality of a juice and/or cider as well as the safety of a juice and/or cider by determining the quantity of microorganisms' DNA present in the juice and/or cider. This invention relates to a novel method of isolating DNA from a juice and/or cider.

Brief Description of the Prior Art

Huanglongbing (HLB) disease in Florida is widespread and associated with *Candidatus Liberibacter asiaticus* (CLas), a phloem limited bacterium. This disease can kill a tree in 5-10 years, and orange juice processed from HLB affected fruit is often associated with bitter taste and/or off-flavor (Baldwin, et al., *J. Agr. Food Chem.* 58:1247-1262 (2010); Plotto, et al., *J. Food Sci.* 75:S220-S230 (2010)). CLas population has been shown to correlate with HLB symptoms in that leaves with serious symptoms had higher CLas population (Gottwald, et al., *Crop Protect.* 36:73-82 (2012); Stover and McCollum, *HortScience* 46:1344-1348 (2011); Trivedi, et al., *European J. Plant Pathol.* 124:553-563 (2009)). *Candidatus Liberibacter africanus* (CLaf) and *Candidatus Liberibacter americanus* (CLam) also cause HLB disease in citrus trees in Africa and Brazil, respectively.

Quantitative polymerase chain reaction (qPCR) is an excellent diagnostic assay tool for determining if a plant is infected with a pathogen. Prior to conducting qPCR, one must first isolate and purify DNA. While many different methods of isolating and purifying DNA exist, in general, the most commonly used methods fall within one of two categories. One category uses SDS to lyse the cells, then uses a high concentration of KoAC to precipitate SDS and protein and thus is referred to as the SDS-KoAC method (Dellaporta, et al., *Plant Molecular Biology Reporter*, 1(4): 19-21 (1983)). The second category uses CTAB in the extraction procedure and thus is referred to as the CTAB method (Allen, et al., *Nat. Protoc.,*1(5):2320-2325 (2006)). Many additional methods exist including, but not limited to, silica-based isolation kits, magnetic particle separation technology, use of resins, etc. One of the difficulties in isolating DNA from plant material and pathogen cells in the presence of rigid polysaccharide cell wall and capsules which physically inhibit DNA liberation (Gonzalez-Mendoza, et al., *Gen. Mol. Res.* 9:162-166 (2010); Noor Adila, et al., *Mal. J. Microbiol.* 3:7-13 (2007); Varma, et al., *Biotechnol. J.* 2:386-392 (2007)). The most widely used method for tissue disruption for DNA extraction from plant tissue has been by grinding tissue with mortar and pestle under liquid nitrogen: the finer the grind, the greater the amount of DNA extracted (Rogstad, et al., *Plant Mol. Biol. Rep.* 19:353-359 (2001)). When the concentration of target DNA is low and the concentration of interfering compounds (e.g., plant cell walls, pectin, other sugars, proteins, secondary metabolites) is high, then additional lysis steps (e.g., mechanical disruption, sonication, enzymatic digestion) and/or additional purification steps (e.g., elution column) may be required (Al-Samarrai and Schmid, *Lett. Appl. Microbiol.* 30:53-56 (2000); Alaey, et al., *Intl. J. Agr. Biol.* 7:882-884 (2005); and Gonzalez-Mendoza, et al. (2010)). However, when one uses orange tree leaves or more precisely, midribs of orange tree leaves, which are rich in phloem vessels that harbor the CLas bacteria, one is able to isolate and purify bacterial DNA without using a sonicator, digestive enzymes or an elution column because the concentration of CLas DNA is high in phloem vessels compared to the concentration of the above described interfering compounds.

In contrast to midribs of leaves, juice vesicles contain a much lower amount of CLas cells (0.25% that of citrus leaf tissue) (Li, et al., *Plant Dis.* 92:854-861 (2008); Liao and Burns, *J. Expt. Bot.* 63:3307-3319 (2012)) and more interfering compounds (e.g., pectin, other sugars and secondary metabolites) (Baldwin et al., (2010)). Orange juice has extremely high pectin content compared to leaves and even other juices, measured as galacturonic acid (0.037-1.433 mg/g), depending on variety and harvest time (Baldwin, et al. (2010)). The pectin and DNA often co-purify when using prior art methods of DNA isolation (Scott and Playford, *BioTechniques* 20:974-978 (1996)). In addition, the other sugars in orange juice (e.g., sucrose, glucose and fructose) interfere with DNA extraction and isolation when using prior art isolation methods (Baldwin, et al. (2010)). A number of DNA extraction methods have been developed to avoid the co-precipitation of pectin/polysaccharides and DNA, including the use of high NaCl concentration (Varma, et al. (2007)) in conjunction with modified cetyl trimethyl ammonium bromide (CTAB) (Shepard and McLay, *J. Plant Res.* 124:311-314 (2011)), phenol, ethylene glycol monoethyl ester and pectinase (Okada, et al., *Amer. J. Bot.* 84:1236:1246 (1997); Rether, et al., *Plant Mol. Biol. Rep.* 11:333-337 (1993); and Rogstad, et al. (2001)). Unfortunately, although the CTAB plus high NaCL concentration method works well for isolating and purifying CLas DNA from citrus leaf tissue which has high CLas DNA concentration, this method does not work well with citrus juice which has low CLas DNA concentration and a high concentration of interfering polysaccharides, especially pectin. Another method uses pectinase to digest the pectin (Bai, et al., in press), however, only low yields of DNA are obtained (see Table 1) perhaps because commercial pectinase preparations contain low levels of DNase. Thus, it is difficult to obtain high quantity and quality DNA (both microorganism's DNA and plant DNA) from citrus juice. In fact, prior attempts to isolate sufficient quantity of DNA at a sufficient purity level from orange juice using Qiagen's DNeasy Plant Mini Kit, Qiagen's mericon Food Kit, Qiagen's QIAamp DNA Blood Mini Kit, or Promega's Wizard® Genomic DNA purification kit were not successful (see infra).

As mentioned above, orange juice is rich in secondary metabolites, including alkaloids, limonoids, and flavonoids, which are not present in high concentrations in leaf tissue relative to CLas DNA (Baldwin, et al. (2010); Justesen, et al., *J. chromatogr. A* 799:101-110 (1998)). These secondary metabolites can inhibit PCR reaction (Deng and Cliver, *Intl. J. Food Microbiol.* 54:155-162 (2000); Kim and Cho, *Food Control* 21:1419-1423 (2000); Ogunjimi and Choudary, *FEMS Immunol. Med. Microbiol.* 23:213-220 (1999); Tsai and Olson, *Appl. Environ. Microbiol.* 58:2292-2295 (1992); Wilson, I. G., *Appl. Environ. Microbiol.* 63:3741-3751

(1997)). Appropriate ion exchange columns or chelating agents can be used to remove these contaminants (Saunders, G. C., *DNA extraction*, p 29-46. In: G. C. Saunders and H. C. Parkers (eds.) *Analytical molecular biology: Quality and validation*. Royal Soc. Chem. Cambridge). Kim and Cho (2010) successfully removed PCR inhibitors from apple, grape, and watermelon juices using Chelex treatment and Sephadex column filtration. However, Kim and Cho were unsuccessful using this method to isolate DNA free from secondary metabolites from orange juice. In contrast, Li, et al. (*J. Microbiol. Meth.* 66:104-115 (2006)) showed that TaqMan® and other commercial "real-time" PCR assays for CLas DNA were not inhibited when the samples were extracted from citrus leaf tissue with the standard cetyl trimethyl ammonium bromide (CTAB) method or the DNeasy® plant kit (Qiagen, Gaithersburg, Md.), indicating that these qPCR assays with a small amplicon (about 70 bp) perhaps are less vulnerable to inhibitors of the amplification reaction in comparison with the conventional PCR assays with a large amplicon (about 1200 bp) (Mackay, et al., *Nucl. Acid. Res.* 30:1292-1305 (2002)). The TaqMan® assay was also used with orange juice and successfully amplified CLas DNA. However, as mentioned previously, these DNA extraction methods yield too low a concentration of DNA to be of practical use. Furthermore, standard deviations of the cycle threshold (Ct) value in qPCT increases as the quantity of target DNA decreases, indicating a higher risk of error at low target DNA concentrations (Liu, et al., *J. Microbiol. Meth.* 65:21-31 (2006)).

In 2013, a new method for detecting CLas DNA in orange juice was disclosed (Bai, et al., *Proc. Fla. State Hort. Soc.* 125:233-238 (2013)), however this method is too complicated for commercial use by citrus processors, uses too much orange juice during the assay, and is not consistently accurate because of the small amount of DNA produced results in an increase of the standard deviation of Ct value. As such, the need still exists for a simple, reliable assay to detect CLas in citrus juice by assaying for CLas DNA in the juice. Furthermore, this method enables one to isolate and purify the DNA of other microorganisms in orange juice and other juices.

Currently, orange juice quality is determined by a U.S. Department of Agriculture grades as determined by an inspector who tastes and grades the juice and by measurement of soluble solids, titratable acidity and sometimes the bitter limonoid, limonin by the juice processors. There is a need for a more quantitative assay to determine whether the quality of a juice has been adversely impacted by a microorganism, and if so, how much has the flavor changed. This assay can also be used to determine if a juice is fit for consumption.

BRIEF DESCRIPTION OF THE INVENTION

It is an object of this invention to have a method for isolating nucleic acids from a liquid, the method involving the steps of separating the solid components present in a sample of the liquid from the liquid soluble components, lysing the cells present in the solid components to release nucleic acids, proteins, polysaccharides, lipids and non-polar material present in the cells, separating the proteins, lipids, and non-polar material from the nucleic acids and polysaccharides, separating the polysaccharides from the nucleic acids, and washing the nucleic acids. It is a further object of this invention that the liquid can be a juice, cider, wine, or other liquid.

It is an object of this invention to have a method for isolating nucleic acids from a liquid, the method involving the steps of separating the solid components present in a sample of the liquid from the liquid soluble components, lysing the cells present in the solid components to release nucleic acids, proteins, polysaccharides, lipids and non-polar material present in the cells, separating the proteins, lipids, and non-polar material from the nucleic acids and polysaccharides, separating the polysaccharides from the nucleic acids, and washing the nucleic acids. It is another object of this invention that the step of separating the polysaccharides from the nucleic acids involves mixing an aqueous solution of CTAB and salt with the polysaccharides and nucleic acids such that the nucleic acids precipitate out of solution of the aqueous solution and such that the polysaccharides remain dissolved in the aqueous solution. It is another object of this invention that the step of separating the polysaccharides from the nucleic acids involves separating the aqueous solution containing the dissolved polysaccharides from the nucleic acids. It is a further object of this invention that the liquid can be a juice, cider, wine, or other liquid.

It is an object of this invention to have a method for isolating nucleic acids from a liquid, the method involving the steps of separating the solid components present in a sample of the liquid from the liquid soluble components, lysing the cells present in the solid components to release nucleic acids, proteins, polysaccharides, lipids and non-polar material present in the cells, separating the proteins, lipids, and non-polar material from the nucleic acids and polysaccharides, separating the polysaccharides from the nucleic acids, and washing the nucleic acids. It is another object of this invention that the step of separating the polysaccharides from the nucleic acids involves mixing an aqueous solution of CTAB and salt with the polysaccharides and nucleic acids such that the nucleic acids precipitate out of solution of the aqueous solution and such that the polysaccharides remain dissolved in the aqueous solution. It is another object of this invention that the step of separating the polysaccharides from the nucleic acids involves separating the aqueous solution containing the dissolved polysaccharides from the nucleic acids. It is a further object of this invention that the concentration of the salt in the aqueous solution is between approximately 10 mM and approximately 400 mM. It is another object of this invention that the salt concentration is between approximately 100 mM and approximately 300 mM. It is yet another object of this invention that the concentration of salt is approximately 250 mM. It is a further object of this invention that the liquid can be a juice, cider, wine, or other liquid.

It is an object of this invention to have a method for isolating nucleic acids from a liquid, the method involving the steps of separating the solid components present in a sample of the liquid from the liquid soluble components, lysing the cells present in the solid components to release nucleic acids, proteins, polysaccharides, lipids and non-polar material present in the cells, separating the proteins, lipids, and non-polar material from the nucleic acids and polysaccharides, separating the polysaccharides from the nucleic acids, and washing the nucleic acids. It is another object of this invention that the mixture of nucleic acids and polysaccharides contains salt. It is another object of this invention that the step of separating the polysaccharides from the nucleic acids involves mixing an aqueous solution of CTAB with the polysaccharides nucleic acids and salt to form a solution. It is another object of this invention that the solution containing CTAB, salt, polysaccharides and nucleic acids have a salt concentration such that the nucleic acids precipitate out of solution of the solution and such that the polysaccharides remain dissolved in the solution. It is another object of this invention that the step of separating the polysaccharides from the nucleic acids involves separating the solution containing the dissolved polysaccharides from the nucleic acids. It is a further object of this invention that the concentration of the salt in the solution containing CTAB, salt, polysaccharides and nucleic acids is between approximately 10 mM and approximately 400 mM. It is another object of this invention that the salt concentration is between approximately 100 mM and approximately 300 mM. It is yet another object of this invention that the concentration of salt is approximately 250 mM. It is a further object of this invention that the liquid can be a juice, cider, wine, or other liquid.

It is an object of this invention to have an improved method for isolating nucleic acids from a liquid having the steps of separating the solid components present in a sample of the liquid from the liquid soluble components, exposing the solid components to a solution of Tris-base, EDTA, salt, PVP40, β-mercaptoethanol, NaOH, and a surfactant to dissolve the solid components and lyse the cells; optionally heating the solution to lyse the cells; adding chloroform to generate an aqueous phase, an interphase, and organic phase, such that the lipids and non-polar material dissolve in the organic phase and such that denatured proteins are in the interface; separating the aqueous phase from the organic phase and the interface; adding CTAB to the aqueous phase, such that the nucleic acids present in the aqueous phase precipitate out of solution from the aqueous phase; optionally heating to assist in precipitation of the nucleic acids; pelleting the precipitate; optionally resuspending the precipitate in ethanol to remove any remaining CTAB yet allow the nucleic acids to remain undissolved in the ethanol; and separating the nucleic acids from the ethanol, such that the separating step involves pelleting the nucleic acids and separating the ethanol from the pelletted nucleic acids. It is a further object of this invention that the step of exposing the solid components to a solution of Tris-base, EDTA, salt, PVP40, β-mercaptoethanol, NaOH, and a surfactant to dissolve the solid components and lyse the cells involves exposing the solid components to a first solution of Tris-base, EDTA, salt, PVP40, and β-mercaptoethanol, and then adding NaOH and the surfactant to the first solution.

It is an object of this invention to have an improved method for isolating nucleic acids from a liquid having the steps of separating the solid components present in a sample of the liquid from the liquid soluble components, exposing the solid components to a solution of Tris-base, EDTA, salt, PVP40, β-mercaptoethanol, NaOH, and a surfactant to dissolve the solid components and lyse the cells; optionally heating the solution to lyse the cells; adding chloroform to generate an aqueous phase, an interphase, and organic phase, such that the lipids and non-polar material dissolve in the organic phase and such that denatured proteins are in the interface; separating the aqueous phase from the organic phase and the interface; adding CTAB to the aqueous phase, such that the nucleic acids present in the aqueous phase precipitate out of solution from the aqueous phase; optionally heating to assist in precipitation of the nucleic acids; pelleting the precipitate; optionally resuspending the precipitate in ethanol to remove any remaining CTAB yet allow the nucleic acids to remain undissolved in the ethanol; and separating the nucleic acids from the ethanol, such that the separating step involves pelleting the nucleic acids and separating the ethanol from the pelletted nucleic acids. It is a further object of this invention that the step of exposing the solid components to a solution of Tris-base, EDTA, salt, PVP40, β-mercaptoethanol, NaOH, and a surfactant to dissolve the solid components and lyse the cells involves exposing the solid components to a first solution of Tris-base, EDTA, salt, PVP40, and β-mercaptoethanol, and then adding NaOH and the surfactant to the first solution. It is a further object of the invention that the salt concentration of the aqueous phase after adding CTAB is between approximately 100 mM and approximately 300 mM. It is yet another object of this invention that the salt concentration of the aqueous phase after adding CTAB is approximately 250 mM. It is a further object of this invention that the liquid can be a juice, cider, wine, or other liquid.

It is another object of this invention to have a method for determining the quality of a juice or cider having the steps of exposing DNA obtained from the juice or cider to a first primer, a second primer, and to a fluorescent composition, such that the sequence of the first primer and the sequence of the second primer are complementary to specific sequences in a microorganism's DNA and bind to the specific sequences in the microorganism's DNA; amplifying the DNA to generate an amplicon such that the amplicon has the first primer's sequence at one end of the amplicon and the reverse complement of the second primer's sequence at the other end of said amplicon; determining the Ct value of the amplified DNA; and comparing the Ct value to one or more known Ct values wherein the one or more known Ct values indicate the quality of the juice or cider. It is another object of the invention that the quality can be flavor, smell, color, safety, or a combination thereof.

It is another object of this invention to have a method for determining the quality of a juice or cider having the steps of exposing DNA obtained from the juice or cider to a first primer, a second primer, and to a fluorescent composition, such that the sequence of the first primer and the sequence of the second primer are complementary to specific sequences in a microorganism's DNA and bind to the specific sequences in the microorganism's DNA; amplifying the DNA to generate an amplicon such that the amplicon has the first primer's sequence at one end of the amplicon and the reverse complement of the second primer's sequence at the other end of said amplicon; determining the Ct value of the amplified DNA; and comparing the Ct value to one or more known Ct values wherein the one or more known Ct values indicate the quality of the juice or cider. When the quality of the juice or cider is flavor, the amount of DNA in the sample (as can be indicated by the Ct value of the amplified DNA), can be correlated to a negative effect on the taste/flavor of the juice or cider. One can then grade the favor quality of the juice by knowing the Ct values and having them compared to one or more known Ct values when the one or more known Ct values indicates the flavor quality of the juice. For instance, if a certain Ct value indicates a poor flavor quality, the juice can be graded accordingly. Typical poor flavor quality descriptors associated with a negative or poor taste of orange juice, for example, include sourness, bitterness or having a metallic taste.

It is another object of this invention to have a method for determining the quality of a juice or cider having the steps of exposing DNA obtained from the juice or cider to a first primer, a second primer, and to a fluorescent composition, such that the sequence of the first primer and the sequence of the second primer are complementary to specific sequences in a microorganism's DNA and bind to the specific sequences in the microorganism's DNA; amplifying the DNA to generate an amplicon such that the amplicon has the first primer's sequence at one end of the amplicon and the reverse complement of the second primer's sequence at the other end of said amplicon; determining the Ct value of the amplified DNA; and comparing the Ct value to one or more known Ct values wherein the one or more known Ct values indicate the quality of the juice or cider. It is a further object of this invention that the fluorescent composition be either an intercalating dye or a composition of a probe linked to a fluorescent dye and a quencher dye such that the probe's sequence is between approximately 15 contiguous nucleotides and approximately 45 contiguous nucleotides of the amplicon's sequence or the reverse complement of the amplicon's sequence. It is another object of the invention that the quality can be flavor, smell, color, safety, or a combination thereof.

It is an object of this invention to have a method for determining the quality of a juice or cider having the steps of exposing DNA obtained from the juice or cider to a first primer, a second primer, and to a fluorescent composition, such that the sequence of the first primer and the sequence of the second primer are complementary to specific sequences in a microorganism's DNA and bind to the specific sequences in the microorganism's DNA; amplifying the DNA to generate an amplicon such that the amplicon has the first primer's sequence at one end of the amplicon and the reverse complement of the second primer's sequence at the other end of said amplicon; determining the Ct value of the amplified DNA; and comparing the Ct value to one or more known Ct values wherein the one or more known Ct values indicate the quality of the juice or cider. It is another object of the invention that the quality can be flavor, smell, color, safety, or a combination thereof. It is another object of this invention that the microorganism is CLas or CLam, that the first primer's sequence is SEQ ID NO: 1, that the second primer's sequence is SEQ ID NO: 2, and that when the CT value is approximately 25 or less, or approximately 28 or less, or approximately 30 or less, the juice or cider's flavor quality is a poor flavor quality. It is an optional object of this invention that the fluorescent composition be either an intercalating dye or a composition of a probe linked to a fluorescent dye and a quencher dye such that the probe's sequence is between approximately 15 contiguous nucleotides and approximately 45 contiguous nucleotides of the amplicon's sequence or the reverse complement of the amplicon's sequence.

It is an object of this invention to have a method for determining the quality of a juice or cider having the steps of isolating nucleic acids from the juice or cider, exposing isolated DNA to a first primer, a second primer, and to a fluorescent composition, such that the sequence of the first primer and the sequence of the second primer are complementary to specific sequences in a microorganism's DNA and bind to the specific sequences in the microorganism's DNA; amplifying the DNA to generate an amplicon such that the amplicon has the first primer's sequence at one end of the amplicon and the reverse complement of the second primer's sequence at the other end of said amplicon; determining the Ct value of the amplified DNA; and comparing the Ct value to one or more known Ct values wherein the one or more known Ct values indicate the quality of the juice or cider. It is another object of the invention that the quality can be flavor, smell, color, safety, or a combination thereof. It is another object of this invention of that the step of isolating nucleic acids from the juice or cider involves separating the solid components present in a sample of the juice or cider from the juice or cider, lysing the cells present in the solid components to release nucleic acids, proteins, polysaccharides, lipids and non-polar material present in the cells, separating the proteins, lipids, and non-polar material from the nucleic acids and polysaccharides, separating the polysaccharides from the nucleic acids, and washing the nucleic acids. It is another object of this invention that the microorganism is CLas or CLam, that the first primer's sequence is SEQ ID NO: 1, that the second primer's sequence is SEQ ID NO: 2, and that when the CT value is approximately 25 or less, or approximately 28 or less, or approximately 30 or less, the juice or cider's flavor quality is a poor flavor quality. It is an optional object of this invention that the fluorescent composition be either an intercalating dye or a composition of a probe linked to a fluorescent dye and a quencher dye such that the probe's sequence is between approximately 15 contiguous nucleotides and approximately 45 contiguous nucleotides of the amplicon's sequence or the reverse complement of the amplicon's sequence.

It is an object of this invention to have a method for determining the quality of a juice or cider having the steps of isolating nucleic acids from the juice or cider, exposing isolated DNA to a first primer, a second primer, and to a fluorescent composition, such that the sequence of the first primer and the sequence of the second primer are complementary to specific sequences in a microorganism's DNA and bind to the specific sequences in the microorganism's DNA; amplifying the DNA to generate an amplicon such that the amplicon has the first primer's sequence at one end of the amplicon and the reverse complement of the second primer's sequence at the other end of said amplicon; determining the Ct value of the amplified DNA; and comparing the Ct value to one or more known Ct values wherein the one or more known Ct values indicate the quality of the juice or cider. It is another object of the invention that the quality can be flavor, smell, color, safety, or a combination thereof. It is another object of this invention of that the step of isolating nucleic acids from the juice or cider involves separating the solid components present in a sample of the juice or cider from the juice or cider, lysing the cells present in the solid components to release nucleic acids, proteins, polysaccharides, lipids and non-polar material present in the cells, separating the proteins, lipids, and non-polar material from the nucleic acids and polysaccharides, mixing an aqueous solution of CTAB and salt with the polysaccharide and nucleic acids such that the nucleic acids precipitate out of the aqueous solution and the polysaccharides remain dissolved in the aqueous solution, separating aqueous solution containing the dissolved polysaccharides from the precipitated nucleic acids, and washing the precipitated nucleic acids. It is another object of this invention that the microorganism is CLas or CLam, that the first primer's sequence is SEQ ID NO: 1, that the second primer's sequence is SEQ ID NO: 2, and that when the CT value is approximately 25 or less, or approximately 28 or less, or approximately 30 or less, the juice or cider's flavor quality is a poor flavor quality. It is an optional object of this invention that the fluorescent composition be either an intercalating dye or a composition of a probe linked to a fluorescent dye and a quencher dye such that the probe's sequence is between approximately 15 contiguous nucleotides and approximately 45 contiguous nucleotides of the amplicon's sequence or the reverse complement of the amplicon's sequence.

It is an object of this invention to have a method for determining the quality of a juice or cider having the steps of exposing DNA obtained from the juice or cider to a first primer, a second primer, and to a fluorescent composition, such that the sequence of the first primer and the sequence of the second primer are complementary to specific sequences in a microorganism's DNA and bind to the specific sequences in the microorganism's DNA; amplifying the DNA to generate an amplicon such that the amplicon has the first primer's sequence at one end of the amplicon and the reverse complement of the second primer's sequence at the other end of said amplicon; determining the Ct value of the amplified DNA; and comparing the Ct value to one or more known Ct values wherein the one or more known Ct values indicate the quality of the juice or cider. It is another object of the invention that the quality can be flavor, smell, color, safety, or a combination thereof. It is another object of this invention that the microorganism is CLas, that the first primer's sequence is SEQ ID NO: 3, that the second primer's sequence is SEQ ID NO: 4, and that when the CT value is approximately 30 or less, approximately 32 or less, or approximately 35 or less, the juice or cider's flavor quality is a poor flavor quality. It is an optional object of this invention that the fluorescent composition be either an intercalating dye or a composition of a probe linked to a fluorescent dye and a quencher dye such that the probe's sequence is between approximately 15 contiguous nucleotides and approximately 45 contiguous nucleotides of the amplicon's sequence or the reverse complement of the amplicon's sequence.

It is an object of this invention to have a method for determining the quality of a juice or cider having the steps of isolating nucleic acids from the juice or cider, exposing isolated DNA to a first primer, a second primer, and to a fluorescent composition, such that the sequence of the first primer and the sequence of the second primer are complementary to specific sequences in a microorganism's DNA and bind to the specific sequences in the microorganism's DNA; amplifying the DNA to generate an amplicon such that the amplicon has the first primer's sequence at one end of the amplicon and the reverse complement of the second primer's sequence at the other end of said amplicon; determining the Ct value of the amplified DNA; and comparing the Ct value to one or more known Ct values wherein the one or more known Ct values indicate the quality of the juice or cider. It is another object of the invention that the quality can be flavor, smell, color, safety, or a combination thereof. It is another object of this invention of that the step of isolating nucleic acids from the juice or cider involves separating the solid components present in a sample of the juice or cider from the juice or cider, lysing the cells present in the solid components to release nucleic acids, proteins, polysaccharides, lipids and non-polar material present in the cells, separating the proteins, lipids, and non-polar material from the nucleic acids and polysaccharides, separating the polysaccharides from the nucleic acids, and washing the nucleic acids. It is another object of this invention that the microorganism is CLas, that the first primer's sequence is SEQ ID NO: 3, that the second primer's sequence is SEQ ID NO: 4, and that when the CT value is approximately 30 or less, or approximately 32 or less, or approximately 35 or less, the juice or cider's flavor quality is a poor flavor quality. It is an optional object of this invention that the fluorescent composition be either an intercalating dye or a composition of a probe linked to a fluorescent dye and a quencher dye such that the probe's sequence is between approximately 15 contiguous nucleotides and approximately 45 contiguous nucleotides of the amplicon's sequence or the reverse complement of the amplicon's sequence.

It is an object of this invention to have a method for determining the quality of a juice or cider having the steps of isolating nucleic acids from the juice or cider, exposing isolated DNA to a first primer, a second primer, and to a fluorescent composition, such that the sequence of the first primer and the sequence of the second primer are complementary to specific sequences in a microorganism's DNA and bind to the specific sequences in the microorganism's DNA; amplifying the DNA to generate an amplicon such that the amplicon has the first primer's sequence at one end of the amplicon and the reverse complement of the second primer's sequence at the other end of said amplicon; determining the Ct value of the amplified DNA; and comparing the Ct value to one or more known Ct values wherein the one or more known Ct values indicate the quality of the juice or cider. It is another object of the invention that the quality can be flavor, smell, color, safety, or a combination thereof. It is another object of this invention of that the step of isolating nucleic acids from the juice or cider involves separating the solid components present in a sample of the juice or cider from the juice or cider, lysing the cells present in the solid components to release nucleic acids, proteins, polysaccharides, lipids and non-polar material present in the cells, separating the proteins, lipids, and non-polar material from the nucleic acids and polysaccharides, mixing an aqueous solution of CTAB and salt with the polysaccharide and nucleic acids such that the nucleic acids precipitate out of the aqueous solution and the polysaccharides remain dissolved in the aqueous solution, separating aqueous solution containing the dissolved polysaccharides from the precipitated nucleic acids, and washing the precipitated nucleic acids. It is another object of this invention that the microorganism is CLas, that the first primer's sequence is SEQ ID NO: 3, that the second primer's sequence is SEQ ID NO: 4, and that when the CT value is approximately 30 or less, or approximately 32 or less, or approximately 35 or less, the juice or cider's flavor quality is a poor flavor quality. It is an optional object of this invention that the fluorescent composition be either an intercalating dye or a composition of a probe linked to a fluorescent dye and a quencher dye such that the probe's sequence is between approximately 15 contiguous nucleotides and approximately 45 contiguous nucleotides of the amplicon's sequence or the reverse complement of the amplicon's sequence.

It is an object of this invention to have a method for determining the quality of a juice or cider having the steps of exposing DNA obtained from the juice or cider to a first primer, a second primer, and to a fluorescent composition, such that the sequence of the first primer and the sequence of the second primer are complementary to specific sequences in a microorganism's DNA and bind to the specific sequences in the microorganism's DNA; amplifying the DNA to generate an amplicon such that the amplicon has the first primer's sequence at one end of the amplicon and the reverse complement of the second primer's sequence at the other end of said amplicon; determining the Ct value of the amplified DNA; and comparing the Ct value to one or more known Ct values wherein the one or more known Ct values indicate the quality of the juice or cider. It is another object of the invention that the quality can be flavor, smell, color, safety, or a combination thereof. It is another object of this invention that the DNA is be obtained from a lactic acid bacteria, an acetic acid bacteria, *Alicyclobacillus* spp., *Zygosaccharomyces* spp., *Rhodotorula ruba*, *Escherichia coli*, *Listeria* spp., *Shigella* spp., *Salmonella* spp., *Klebsiella* spp., *Candidatus Liberibacter asiaticus* (CLas), *Candidatus Liberibacter africanus* (CLaf), and *Candidatus Liberibacter americanus* (CLam).

It is an object of this invention to have a method for identifying the quantity of a microorganism in a liquid having the steps of exposing DNA obtained from the liquid to a first primer, a second primer, and to a fluorescent composition, such that the first primer's sequence and the second primer's sequence are complementary to specific sequences in a microorganism's DNA and bind to those specific sequences; amplifying the DNA to generate an amplicon such that the amplicon's sequence at one end is the same as the first primer's sequence and the amplicon's sequence at the other end is the same as the reverse complement of the second primer's sequence; determining the Ct value of the amplified DNA; and comparing the Ct value to one or more known Ct values such that the one or more known Ct values indicate the quantity of the microorganism in the liquid. It is a further object of this invention that the liquid can be a juice, cider, wine, or other liquid.

It is another object of this invention to have a method for identifying the quantity of a microorganism in a liquid having the steps of exposing DNA obtained from the liquid to a first primer, a second primer, and to a fluorescent composition, such that the first primer's sequence and the second primer's sequence are complementary to specific sequences in a microorganism's DNA and bind to those specific sequences; amplifying the DNA to generate an amplicon such that the amplicon's sequence at one end is the same as the first primer's sequence and the amplicon's sequence at the other end is the same as the reverse complement of the second primer's sequence; determining the Ct value of the amplified DNA; and comparing the Ct value to one or more known Ct values such that the one or more known Ct values indicate the quantity of the microorganism in the liquid. It is a further object of this invention that the liquid can be a juice, cider, wine, or other liquid. It is a further object of this invention that the fluorescent composition be either an intercalating dye or a composition of a probe linked to a fluorescent dye and a quencher dye, and that the probe's sequence is between approximately 15 contiguous nucleotides and approximately 45 contiguous nucleotides of the amplicon's sequence or the reverse complement of the amplicon's sequence.

It is an object of this invention to have a method for identifying the quantity of a microorganism in a liquid having the steps of exposing DNA obtained from the liquid to a first primer, a second primer, and to a fluorescent composition, such that the first primer's sequence and the second primer's sequence are complementary to specific sequences in a microorganism's DNA and bind to those specific sequences; amplifying the DNA to generate an amplicon such that the amplicon's sequence at one end is the same as the first primer's sequence and the amplicon's sequence at the other end is the same as the reverse complement of the second primer's sequence; determining the Ct value of the amplified DNA; and comparing the Ct value to one or more known Ct values such that the one or more known Ct values indicate the quantity of the microorganism in the liquid. It is a further object of this invention that the liquid can be a juice, cider, wine, or other liquid. It is another object of this invention that the microorganism be a lactic acid bacteria, an acetic acid bacteria, *Alicyclobacillus* spp., *Zygosaccharomyces* spp., *Rhodotorula ruba*, *Escherichia coli*, *Listeria* spp., *Shigella* spp., *Salmonella* spp., *Klebsiella* spp., *Candidatus Liberibacter asiaticus* (CLas), *Candidatus Liberibacter africanus* (CLaf), and *Candidatus Liberibacter americanus* (CLam).

It is an object of this invention to have a method for identifying the quantity of a microorganism in a liquid having the steps of exposing DNA obtained from the liquid to a first primer, a second primer, and to a fluorescent composition, such that the first primer's sequence and the second primer's sequence are complementary to specific sequences in a microorganism's DNA and bind to those specific sequences; amplifying the DNA to generate an amplicon such that the amplicon's sequence at one end is the same as the first primer's sequence and the amplicon's sequence at the other end is the same as the reverse complement of the second primer's sequence; determining the Ct value of the amplified DNA; and comparing the Ct value to one or more known Ct values such that the one or more known Ct values indicate the quantity of the microorganism in the liquid. It is a further object of this invention that the liquid can be a juice, cider, wine, or other liquid. It is another object of this invention that the microorganism be a lactic acid bacteria, an acetic acid bacteria, *Alicyclobacillus* spp., *Zygosaccharomyces* spp., *Rhodotorula ruba*, *Escherichia coli*, *Listeria* spp., *Shigella* spp., *Salmonella* spp., *Klebsiella* spp., *Candidatus Liberibacter asiaticus* (CLas), *Candidatus Liberibacter africanus* (CLaf), and *Candidatus Liberibacter americanus* (CLam). It is a further object of this invention that the fluorescent composition is either an intercalating dye or a composition of a probe linked to a fluorescent dye and a quencher dye, and that the probe's sequence is between approximately 15 contiguous nucleotides and approximately 45 contiguous nucleotides of the amplicon's sequence or the reverse complement of the amplicon's sequence.

It is an object of this invention to have a method for identifying the quantity of CLas or CLam in a liquid having the steps of exposing DNA obtained from the liquid to a first primer, a second primer, and to a fluorescent composition, such that the first primer's sequence and the second primer's sequence are complementary to specific sequences in CLas' DNA or CLam's DNA and bind to those specific sequences; amplifying the DNA to generate an amplicon such that the amplicon's sequence at one end is the same as the first primer's sequence and the amplicon's sequence at the other end is the same as the reverse complement of the second primer's sequence; determining the Ct value of the amplified DNA; and comparing the Ct value to one or more known Ct values such that the one or more known Ct values indicate the quantity of the microorganism in the liquid. It is a further object of this invention that the liquid can be a juice, cider, wine, or other liquid. It is another object of this invention that the first primer's sequence is SEQ ID NO: 1 and the second primer's sequence is SEQ ID NO: 2, and that which the Ct value is approximately 25 or less, or approximately 28 or less, or approximately 30 or less, then the amount of CLas or CLam in the liquid is too high. It is optional to have another object of this invention that the fluorescent composition is either an intercalating dye or a composition of a probe linked to a fluorescent dye and a quencher dye, and that the probe's sequence is between approximately 15 contiguous nucleotides and approximately 45 contiguous nucleotides of the amplicon's sequence or the reverse complement of the amplicon's sequence.

It is an object of this invention to have a method for identifying the quantity of CLas or CLam in a liquid having the steps of isolating nucleic acids from the liquid, exposing DNA obtained from the liquid to a first primer, a second primer, and to a fluorescent composition, such that the first primer's sequence and the second primer's sequence are complementary to specific sequences in CLas' DNA or CLam's DNA and bind to those specific sequences; amplifying the DNA to generate an amplicon such that the amplicon's sequence at one end is the same as the first primer's sequence and the amplicon's sequence at the other end is the same as the reverse complement of the second primer's sequence; determining the Ct value of the amplified DNA; and comparing the Ct value to one or more known Ct values such that the one or more known Ct values indicate the quantity of the microorganism in the liquid. It is a further object of this invention that the liquid can be a juice, cider, wine, or other liquid. It is another object of this invention that the first primer's sequence is SEQ ID NO: 1 and the second primer's sequence is SEQ ID NO: 2, and that which the Ct value is approximately 25 or less, approximately 28 or less, or approximately 30 or less, then the amount of CLas or CLam in the liquid is too high. It is a further object of this invention that the step of isolating nucleic acids from the liquid involves separating the solid components present in a sample of the liquid from the liquid, lysing the cells present in the solid components to release nucleic acids, proteins, polysaccharides, lipids and non-polar material present in the cells, separating the proteins, lipids, and non-polar material from the nucleic acids and polysaccharides, separating the polysaccharides from the nucleic acids, and washing the nucleic acids. It is optional to have another object of this invention that the fluorescent composition is either an intercalating dye or a composition of a probe linked to a fluorescent dye and a quencher dye, and that the probe's sequence is between approximately 15 contiguous nucleotides and approximately 45 contiguous nucleotides of the amplicon's sequence or the reverse complement of the amplicon's sequence.

It is an object of this invention to have a method for identifying the quantity of CLas or CLam in a liquid having the steps of isolating nucleic acids from the liquid, exposing DNA obtained from the liquid to a first primer, a second primer, and to a fluorescent composition, such that the first primer's sequence and the second primer's sequence are complementary to specific sequences in CLas' DNA or CLam's DNA and bind to those specific sequences; amplifying the DNA to generate an amplicon such that the amplicon's sequence at one end is the same as the first primer's sequence and the amplicon's sequence at the other end is the same as the reverse complement of the second primer's sequence; determining the Ct value of the amplified DNA; and comparing the Ct value to one or more known Ct values such that the one or more known Ct values indicate the quantity of the microorganism in the liquid. It is a further object of this invention that the liquid can be a juice, cider, wine, or other liquid. It is another object of this invention that the first primer's sequence is SEQ ID NO: 1 and the second primer's sequence is SEQ ID NO: 2, and that which the Ct value is approximately 25 or less, approximately 28 or less, or approximately 30 or less, then the amount of CLas or CLam in the liquid is too high. It is another object of this invention of that the step of isolating nucleic acids from the liquid involves separating the solid components present in a sample of the liquid from the liquid soluble components, lysing the cells present in the solid components to release nucleic acids, proteins, polysaccharides, lipids and non-polar material present in the cells, separating the proteins, lipids, and non-polar material from the nucleic acids and polysaccharides, mixing an aqueous solution of CTAB and salt with the polysaccharide and nucleic acids such that the nucleic acids precipitate out of the aqueous solution and the polysaccharides remain dissolved in the aqueous solution, separating aqueous solution containing the dissolved polysaccharides from the precipitated nucleic acids, and washing the precipitated nucleic acids. It is optional to have another object of this invention that the fluorescent composition is either an intercalating dye or a composition of a probe linked to a fluorescent dye and a quencher dye, and that the probe's sequence is between approximately 15 contiguous nucleotides and approximately 45 contiguous nucleotides of the amplicon's sequence or the reverse complement of the amplicon's sequence.

It is an object of this invention to have a method for identifying the quantity of CLas in a liquid having the steps of exposing DNA obtained from the liquid to a first primer, a second primer, and to a fluorescent composition, such that the first primer's sequence and the second primer's sequence are complementary to specific sequences in CLas' DNA and bind to those specific sequences; amplifying the DNA to generate an amplicon such that the amplicon's sequence at one end is the same as the first primer's sequence and the amplicon's sequence at the other end is the same as the reverse complement of the second primer's sequence; determining the Ct value of the amplified DNA; and comparing the Ct value to one or more known Ct values such that the one or more known Ct values indicate the quantity of the microorganism in the liquid. It is a further object of this invention that the liquid can be a juice, cider, wine, or other liquid. It is another object of this invention that the first primer's sequence is SEQ ID NO: 3 and the second primer's sequence is SEQ ID NO: 4, and that which the Ct value is approximately 30 or less, approximately 32 or less, or approximately 35 or less, then the amount of CLas in the liquid is too high. It is optional to have another object of this invention that the fluorescent composition is either an intercalating dye or a composition of a probe linked to a fluorescent dye and a quencher dye, and that the probe's sequence is between approximately 15 contiguous nucleotides and approximately 45 contiguous nucleotides of the amplicon's sequence or the reverse complement of the amplicon's sequence.

It is an object of this invention to have a method for identifying the quantity of CLas in a liquid having the steps of isolating nucleic acids from the liquid, exposing DNA obtained from the liquid to a first primer, a second primer, and to a fluorescent composition, such that the first primer's sequence and the second primer's sequence are complementary to specific sequences in CLas' DNA and bind to those specific sequences; amplifying the DNA to generate an amplicon such that the amplicon's sequence at one end is the same as the first primer's sequence and the amplicon's sequence at the other end is the same as the reverse complement of the second primer's sequence; determining the Ct value of the amplified DNA; and comparing the Ct value to one or more known Ct values such that the one or more known Ct values indicate the quantity of the microorganism in the liquid. It is a further object of this invention that the liquid can be a juice, cider, wine, or other liquid. It is another object of this invention that the first primer's sequence is SEQ ID NO: 3 and the second primer's sequence is SEQ ID NO: 4, and that which the Ct value is approximately 30 or less, approximately 32 or less, or approximately 35 or less, then the amount of CLas in the liquid is too high. It is a further object of this invention that the step of isolating nucleic acids from the liquid involves separating the solid components present in a sample of the liquid from the liquid soluble components, lysing the cells present in the solid components to release nucleic acids, proteins, polysaccharides, lipids and non-polar material present in the cells, separating the proteins, lipids, and non-polar material from the nucleic acids and polysaccharides, separating the polysaccharides from the nucleic acids, and washing the nucleic acids. It is optional to have another object of this invention that the fluorescent composition is either an intercalating dye or a composition of a probe linked to a fluorescent dye and a quencher dye, and that the probe's sequence is between approximately 15 contiguous nucleotides and approximately 45 contiguous nucleotides of the amplicon's sequence or the reverse complement of the amplicon's sequence.

It is an object of this invention to have a method for identifying the quantity of CLas in a liquid having the steps of isolating nucleic acids from the liquid, exposing DNA obtained from the liquid to a first primer, a second primer, and to a fluorescent composition, such that the first primer's sequence and the second primer's sequence are complementary to specific sequences in CLas' DNA and bind to those specific sequences; amplifying the DNA to generate an amplicon such that the amplicon's sequence at one end is the same as the first primer's sequence and the amplicon's sequence at the other end is the same as the reverse complement of the second primer's sequence; determining the Ct value of the amplified DNA; and comparing the Ct value to one or more known Ct values such that the one or more known Ct values indicate the quantity of the microorganism in the liquid. It is a further object of this invention that the liquid can be a juice, cider, wine, or other liquid. It is another object of this invention that the first primer's sequence is SEQ ID NO: 3 and the second primer's sequence is SEQ ID NO: 4, and that which the Ct value is approximately 30 or less, approximately 32 or less, or approximately 35 or less, then the amount of CLas in the liquid is too high. It is another object of this invention of that the step of isolating nucleic acids from the liquid involves separating the solid components present in a sample of the liquid from the liquid soluble components, lysing the cells present in the solid components to release nucleic acids, proteins, polysaccharides, lipids and non-polar material present in the cells, separating the proteins, lipids, and non-polar material from the nucleic acids and polysaccharides, mixing an aqueous solution of CTAB and salt with the polysaccharide and nucleic acids such that the nucleic acids precipitate out of the aqueous solution and the polysaccharides remain dissolved in the aqueous solution, separating aqueous solution containing the dissolved polysaccharides from the precipitated nucleic acids, and washing the precipitated nucleic acids. It is optional to have another object of this invention that the fluorescent composition is either an intercalating dye or a composition of a probe linked to a fluorescent dye and a quencher dye, and that the probe's sequence is between approximately 15 contiguous nucleotides and approximately 45 contiguous nucleotides of the amplicon's sequence or the reverse complement of the amplicon's sequence.

It is an object of this invention to have a method for determining if a juice or cider is unsafe for consumption having the steps of exposing DNA obtained from the juice or cider to a first primer, a second primer, and to a fluorescent composition, such that the first primer's sequence and the second primer's sequence are complementary to specific sequences in a microorganism's DNA and bind to those specific sequences; amplifying the DNA to generate an amplicon such that the amplicon's sequence at one end is the same as the first primer's sequence and the amplicon's sequence at the other end is the same as the reverse complement of the second primer's sequence; determining the Ct value of the amplified DNA; and comparing the Ct value to one or more known Ct values such that the one or more known Ct values indicate the juice or cider contain too much of the microorganism and is unsafe for consumption.

It is an object of this invention to have a method for determining if a juice or cider is unsafe for consumption having the steps of exposing DNA obtained from the juice or cider to a first primer, a second primer, and to a fluorescent composition, such that the first primer's sequence and the second primer's sequence are complementary to specific sequences in a microorganism's DNA and bind to those specific sequences; amplifying the DNA to generate an amplicon such that the amplicon's sequence at one end is the same as the first primer's sequence and the amplicon's sequence at the other end is the same as the reverse complement of the second primer's sequence; determining the Ct value of the amplified DNA; and comparing the Ct value to one or more known Ct values such that the one or more known Ct values indicate the juice or cider contain too much of the microorganism and is unsafe for consumption. It is a further object of this invention that the fluorescent composition is either an intercalating dye or a composition of a probe linked to a fluorescent dye and a quencher dye, and that the probe's sequence is between approximately 15 contiguous nucleotides and approximately 45 contiguous nucleotides of the amplicon's sequence or the reverse complement of the amplicon's sequence.

It is an object of this invention to have a method for determining if a juice or cider is unsafe for consumption having the steps of exposing DNA obtained from the juice or cider to a first primer, a second primer, and to a fluorescent composition, such that the first primer's sequence and the second primer's sequence are complementary to specific sequences in a microorganism's DNA and bind to those specific sequences; amplifying the DNA to generate an amplicon such that the amplicon's sequence at one end is the same as the first primer's sequence and the amplicon's sequence at the other end is the same as the reverse complement of the second primer's sequence; determining the Ct value of the amplified DNA; and comparing the Ct value to one or more known Ct values such that the one or more known Ct values indicate the juice or cider contain too much of the microorganism and is unsafe for consumption. It is a further object of this invention that the microorganism can be a lactic acid bacteria, an acetic acid bacteria, *Alicyclobacillus* spp., *Zygosaccharomyces* spp., *Rhodotorula ruba*, *Escherichia coli*, *Listeria* spp., *Shigella* spp., *Salmonella* spp., *Klebsiella* spp., *Candidatus Liberibacter asiaticus* (CLas), *Candidatus Liberibacter africanus* (CLaf), and *Candidatus Liberibacter americanus* (CLam).

It is an object of this invention to have a method for determining the quality of a juice or cider having the steps of quantifying the amount of nucleic acids in the juice or cider belonging to one or more microorganisms that impacts the quality of the juice or cider by being present in the juice or cider or by infecting the plant from which the juice or cider is produced, and comparing the amount of nucleic acids in the juice or cider that belong to one or more microorganisms with known values that indicate the quality of the juice or cider. It is another object of the invention that the quantifying step includes amplifying the nucleic acids in the juice or cider belonging to the one or more microorganisms and measuring the amount of the amplified nucleic acids. It is another object of the invention that the quality can be flavor, smell, color, safety, or a combination thereof.

It is another object of this invention to have a method of determining if the quantity of a microorganism is too high in a juice or cider having the steps of quantifying the amount of the microorganism's nucleic acids in the juice or cider and comparing the amount of the microorganism's nucleic acids present in the juice or cider with known values that indicate the quantity of the microorganism. It is yet a further object of the invention that the quantifying step includes amplifying the microorganism's nucleic acids in the juice or cider and measuring the amount of the amplified nucleic acids.

It is a further object of this invention to have a method of determining if a juice or cider is unsafe for consumption by quantifying the amount of one or more microorganisms' nucleic acids present in the juice or cider and comparing the amount of the one or more microorganisms' nucleic acids present in the juice or cider with known values that indicate the safety of the juice or cider for consumption. It is yet another object of the invention that the quantifying step includes amplifying the one or more microorganism's nucleic acids in the juice or cider and measuring the amount of the amplified nucleic acids.

DETAILED DESCRIPTION OF THE INVENTION

Figure 1:
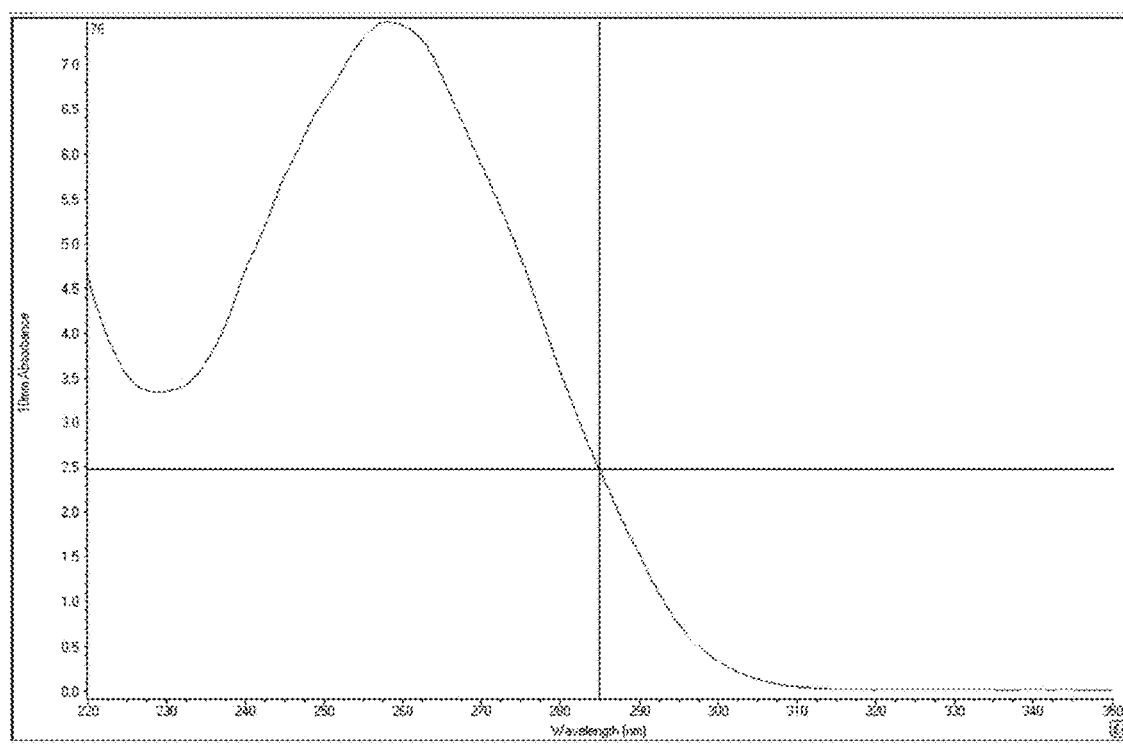
FIG. 1 illustrates a Nano-Drop Spectrophotometer (ThermoFisher Scientific, Waltham, Mass.) reading of isolated and purified DNA extracted from 0.5 ml orange juice and finally dissolved in 30 μl of water.

A need exists for a simple DNA isolation method that yields sufficient highly purified DNA from juice or cider while using small quantity of juice or cider and not using environmentally harsh reagents. Furthermore, there is a need to be able to determine the quality and/or safety of juice and/or cider by assaying the DNA purified by this method or any other DNA purification method. The quality of the juice or cider can be flavor, smell, color, safety, taste, mouth feel, and aftertaste, or a combination thereof. In one embodiment, this method of determining the quality and/or safety of a juice and/or cider uses any method for quantifying the amount of one or more microorganisms' nucleic acids present in the juice and/or cider. In a second embodiment, this method uses polymerase chain reaction (PCR) amplification to quantify the amount of one or more microorganisms' nucleic acids present in the juice and/or cider. In a third embodiment, this method uses quantitative PCR (qPCR) to quantify the amount of one or more microorganisms' nucleic acids present in the juice and/or cider by obtaining the threshold cycle (Ct) value for one or more microorganisms' nucleic acids present in the juice and/or cider. The obtained Ct value is compared to a known Ct value which indicates (1) the juice and/or cider is safe for consumption and/or (2) the juice and/or cider's quality is impaired. After obtaining a Ct value for the juice or cider, one can grade the juice or cider (based on the liquid's qualities) by comparing the obtained Ct value to known Ct values. Surprisingly, the novel methods of this invention work with unpasteurized juices and ciders, as well as with pasteurized juices and ciders. By "safety", it is meant that the juice and/or cider is safe for consumption by humans or other animals. By "determining the quality" refers to determining if the quality of the juice and/or cider has been adversely impacted by a microorganism's presence in or infection of the plant or fruit or contamination of the juice and/or cider. The quality characteristics of a juice or cider include, but are not limited to, flavor, taste, mouth feel, aftertaste, color, and smell. For citrus juices, flavor qualities/descriptors include orange, grapefruit, fruity-non-citrus, orange peel, green, stale, oxidized oil and typical HLB off-flavor; taste quality/descriptors include sweetness, sourness, umami, bitterness and metallic; mouth feel qualities/descriptors include body, tingling, astringent, and burning; and aftertaste qualities/descriptors include bitter and astringent burning. For juices and ciders made from non-citrus fruit, the flavor, mouth feel, and aftertaste qualities can be similar to some or all of the qualities for citrus juices.

The novel methods of this invention can be used on juice or cider obtained from any fruit or vegetable. Non-limiting examples of fruit and vegetables include orange, grapefruit, lemon, lime, apple, grape, pear, peach, plum, pomegranate, celery, cucumber, onion, carrot, lettuce, spinach, beets, watercress, rhubarb, pumpkin, and tomato. For simplicity, the term "fruit" refers to both fruits and vegetables.

Fresh squeezed juices and ciders may be contaminated with harmful microorganisms (harmful to the animal (including human) consuming the liquid or harmful to the plant and/or fruit). These pathogens remain in the juice or cider because the juice or cider does not undergo pasteurization. As such, a need exists to be able to assay for these harmful microorganisms. Nucleic acid amplification assays are highly sensitive and extremely accurate methods of determining the presence or absence of an organism's nucleic acids in a sample. As such, it would be useful to have a nucleic acid amplification assay to determine if these harmful microorganisms' nucleic acids are present in the juice or cider and to be able to determine if the amount of nucleic acids present indicate that the amount of microorganisms are harmful (either to the animal consuming the juice or cider, or to the plant from which the juice or cider was obtained). Further, a need exists for nucleic acid isolation method which can obtain sufficiently pure nucleic acids in sufficient quantity from juice or cider. One reason for this need is to determine if the pasteurization process kills sufficient quantity of the microorganisms. Also, it is possible that even though sufficient numbers of microorganisms are killed during pasteurization, the dead microorganisms or their metabolites alter the quality (flavor, taste, smell, color, safety, mouth feel, and aftertaste or a combination thereof) of the juice or cider. A third reason is that a pasteurized juice or cider can become contaminated with microorganisms after pasteurization, thereby adversely affecting the quality and/or safety of the juice or cider. One can utilize any method to isolate nucleic acids or the nucleic acid isolation method described herein to obtain the nucleic acids from the liquid in a cost-effective manner. Then one can perform any assay which quantifies the amount of nucleic acids present. Alternatively, one can perform PCR to amplify the amount of one or more microorganisms' nucleic acids. Or, alternatively, one can perform qPCR on the isolated nucleic acids using primers that are specific for the one or more microorganism for which one is screening. Next one determines the Ct value, and by comparing the obtained Ct value to a known Ct value, one can determine if the juice or cider is safe to consume or if the quality of the juice or cider (e.g., flavor, taste, smell, mouth feel, aftertaste, or color) has been adversely impacted. One can assign grades to the juice or cider based on the Ct value obtained by performing qPCR on a sample of the liquid and comparing the obtained Ct value to known values which indicate the quality of the juice or cider for a particular quality or safety. Non-limiting examples of pathogens that may exist in juices or ciders include *Escherichia coli, Listeria* spp., *Shigella* spp., *Salmonella* spp., *Klebsiella* spp., *Candidatus Liberibacter asiaticus* (CLas), *Candidatus Liberibacter africanus* (CLaf), and *Candidatus Liberibacter americanus* (CLam).

CLas, CLaf, and CLam cause HLB disease in citrus trees. The juice obtained from the fruit of infected trees can have an "off" taste. Prior art methods of determining the quality of juice is to have people taste the juice and/or measure soluble solids (mostly sugars) and titratable acids. However, these prior art assays do not cover all the off-flavor characteristics imparted by the bacterial disease. There is a need for a quantitative and fast method for assessing the quality of the juice. One can use the nucleic acids isolation methods described herein, or any other isolation method, to isolate the nucleic acids present in the juice. Then one can use any nucleic acid quantification method, or alternatively, can use any nucleic acid amplification method, or alternatively performs qPCR on the isolated nucleic acids to quantify the amount of *Candidatus Liberbacter* nucleic acids present in the juice. Based on the quantify of *Candidatus Liberbacter* nucleic acids present in the juice, one can determine if the quality of the juice has been adversely impacted by the *Candidatus Liberbacter* infection and the degree of impact. To determine the quantify of *Candidatus Liberbacter* present in the juice using qPCR, and possibly other DNA quantification methods, one uses primers specific for the particular *Candidatus Liberbacter* species for which one is assaying, or use a universal primer that will bind to any *Candidatus Liberbacter* species. Then, for qPCR, one determines the Ct value of the amplified DNA and compares the obtained value to a known Ct value to determine the quality of the juice. The quality can be flavor, smell, color, safety, taste, mouth feel, aftertaste, or a combination thereof.

In addition, other microorganisms present on the fruit, in the juice, or in a tree can decrease the quality of the juice obtained from fruit. One can use the methods of this invention to isolate DNA from the juice and determine the quality of the juice. Non-limiting examples of such microorganism include lactic acid bacteria (Parish, M E, *Food Technol.* 45(4):128-132 (1991)), acetic acid bacteria (Murdock, DI, *Microbiology of Citrus Products* (Chap. 11) in *Citrus Science and Technology* v2 Shaw and Veldhuis (eds) Westport, Conn. (1977)), *Alicyclobacillus* spp. (Pettipher, et al., *Letters in Applied Microbiology* 24:185-189 (1997)), *Zygosaccharomyces* spp. (Arias, et al., *Appl. Environ. Microb.* 68:1955-1961 (2002)), and *Rhodotorula ruba* (Sutherland, et al., *J. Food Protection* 58(11):1260-1262 (1995)). Non-limiting examples of lactic acid bacteria are *Lactobacillus* spp., *Leuconostoc* spp., *Pediococcus* spp., *Lactococcus* spp., *Streptococcus* spp., *Aerococcus* spp., *Carnobacterium* spp., *Enterococcus* spp., *Oenococcus* spp., *Sporolactobacillus* spp., *Tetragenococcus* spp., *Vagococcus* spp., and *Weisella* spp. Non-limiting examples of acetic acid bacteria are *Acetobacter* spp., *Acidicaldus* spp., *Acidiphilium* spp., *Acidisphaera* spp., *Acidocella* spp., *Acidomonas* spp., *Asaia* spp., *Belnapia* spp., *Craurococcus* spp., *Gluconacetobacter* spp., *Gluconobacter* spp., *Granulibacter* spp., *Kozakia* spp., *Leahibacter* spp., *Muricoccus* spp., *Neoasaia* spp., *Oleomonas* spp., *Paracraurococcus* spp., *Rhodopila* spp., *Roseococcus* spp., *Rubritepida* spp., *Saccharibacter* spp., *Stella* spp., *Swaminathania* spp., *Teichococcus* spp., and *Zavarzinia* spp.

The quality of the juice can be determined by quantifying the amount of the microorganism's nucleic acids which can be used to determine the adverse impact of the microorganism had on the juice's quality. One can use any method to isolate nucleic acids present in the juice or the method described herein. After the nucleic acids have been isolated, in one embodiment, one can use any method for quantifying the amount of a microorganism's nucleic acid present in the isolated nucleic acids. In another embodiment, one can use any nucleic acid amplification method to quantify the amount of the microorganism's nucleic acids present in the isolated nucleic acids. In another embodiment, one can use qPCR to quantify the amount of the microorganism's nucleic acids present in the isolated nucleic acids. After quantifying the amount of a microorganism's nucleic acids present in the isolated nucleic acids, one can determine the quality of the juice or cider.

Microorganism-specific primers for qPCR or for other nucleic acid amplification methods can be generated based on each microorganism's nucleic acids sequences. For qPCR, each primer set should generate an amplicon of a specific size, and the amplicon's nucleotide sequence should be specific to the microorganism. In general, the amplicon generated by qPCR can range from approximately 70 bp to approximately 250 bp. In one embodiment, the amplicon can range in size between approximately 100 bp to approximately 200 bp. In another embodiment, the amplicon can range in size between 125 bp and 180 bp.

One aspect of this invention involves a novel method for isolating nucleic acids which are present in a liquid, where the liquid can be a juice, a cider, a fermented beverage, or any other liquid obtained from a fruit or vegetable. This nucleic acid isolation method involves separating the solid components (plant material and microorganism material) from the liquid (or from the liquid soluble components), lysing the cells present in the solid components to release nucleic acids and other cellular components, and separating the non-nucleic acid cellular components (proteins, polysaccharides, salts, lipids, etc.) from the nucleic acids.

In another embodiment, one separates the solid components (plant material and microorganism material) from the liquid (or from the liquid soluble components) by centrifuging the liquid so that a pellet of solid components is formed and then decanting the liquid from the tube, leaving the pellet of solid components in the tube. Next, one resuspends the solid components in the tube using the extraction buffer. The extraction buffer contains various chemicals (Tris-base, EDTA, a salt (NaCl or other similar salts), polyvinylpyrrolidone, and water) to help disperse the solid components throughout the extraction buffer and to protect nucleic acids from degradation at a generally neutral or slightly basic pH. The extraction buffer also contains β-mercaptoethanol which helps lyse the cells. Then one adds additional chemicals (NaOH and a surfactant (non-ionic surfactant or cationic surfactant)) that further assist in lysing the cells to the tube containing the extraction buffer and the resuspended material. After thoroughly mixing, one can optionally heat the mixture to assist in lysing the cells. Next, one adds chloroform or a similar compound (such as chloroform and isoamylalcohol or phenol and chloroform) to create an organic phase, an interface, and an aqueous phase, thereby separating out the proteins, lipids, and non-polar compounds from the nucleic acids present in the tube. The denatured proteins are present in the interface; the lipids and non-polar compounds are in the organic phase; and the nucleic acids and polysaccharides are present in the aqueous phase. One may optionally mix the contents of the tube to assist in the dissolution of substances into the organic phase. Then one may optionally centrifuge the tube to separate the aqueous phase from the organic phase and the interface. Next one separates the aqueous phase from the organic phase and interface; but alternatively one can separate the organic phase and interface from the aqueous phase. In some embodiments, one puts the aqueous phase into a new tube. Then one adds hexadecetyl trimethyl ammonium bromide (CTAB) to the aqueous phase and mixes thoroughly. The salt concentration of the aqueous solution containing CTAB can be approximately 400 mM or less. One can optionally heat the aqueous solution containing CTAB. CTAB helps precipitate nucleic acids when the salt concentration is approximately 400 mM or less, yet the polysaccharides (including pectin) present in the aqueous phase remains dissolved in the aqueous phase. Thus, the addition of CTAB into the aqueous phase at the appropriate salt concentration allows one to separate nucleic acids from polysaccharides. Next one can separate the nucleic acids from the aqueous solution containing CTAB and polysaccharides by centrifuging the tube to pellet the nucleic acids and then separating the liquid from the pellet, leaving the isolated nucleic acids in the tube. In some embodiments, one may want to wash the isolated nucleic acids in alcohol (or a solution of alcohol and other liquids) to remove any remaining salts and any CTAB that may be present with the isolated nucleic acids. To wash the nucleic acids, one adds alcohol, resuspends the isolated nucleic acids pellet, then centrifuges the tube to pellet the isolated nucleic acids and decants the alcohol. Again, in some embodiments, one may dissolve the pelletted, isolated nucleic acids in a salt solution for further purification of the nucleic acids using alcohol. Optional heating the solution helps dissolve the nucleic acids. Next one adds alcohol (such as 2-propanol) to the tube and mixes. Then one centrifuges the tube to pellet the nucleic acids (which do not dissolve in the alcohol) and decants the solution of salt and alcohol from the pelletted, isolated nucleic acids. Next, one can optionally remove any remaining salts and other compounds from the isolated nucleic acids by resuspending the pelletted, isolated nucleic acids again in alcohol (such as ethanol) (or a solution of alcohol and other liquids) and then centrifuging again and then decanting the liquid from the pelletted, isolated nucleic acids. One then has highly purified, isolated nucleic acids in a pellet at the bottom of a tube, and one can resuspend the nucleic acids in the any desired liquid (e.g., nuclease-free water).

In one embodiment, one first separates the liquid soluble components from the solid components of the juice or cider (or vice versa). Various methods of separating out the liquid soluble components and the solid components of juice are known in the art. Centrifugation followed by retention of the pellet (the solid components) is one method of separating the two components. Next one adds the appropriate amount of extraction buffer (described infra) and β-mercaptoethanol to the isolated solid components. In an alternative embodiment, one first makes the extraction buffer (described infra). Then one separates the solid components and the liquid soluble components in the juice. And then one adds β-mercaptoethanol to the extraction buffer prior to adding of the extraction buffer to the isolated solid components.

In one embodiment, one liter of the extraction buffer contains approximately 12.1 g Tris-base (final concentration: approximately 100 mM), approximately 18.61 g EDTA (final concentration: approximately 50 mM), approximately 29.22 g NaCl (final concentration: approximately 500 mM), approximately 25 g polyvinylpyrrolidone (PVP40) (final concentration: approximately 2.5%), and approximately 800 mL water to dissolve the components. The pH of the extraction buffer is adjusted, if necessary, by adding sufficient 1 M HCl or 1 M NaOH to bring the pH to approximately 8.0. One adds sufficient water to bring the total volume to one liter. One adds approximately 2 μL of β-mercaptoethanol per ml of extraction buffer (the final β-mercaptoethanol concentration is approximately 0.2% (v/v)) to the extraction buffer immediately prior to using the extraction buffer. In an alternative embodiment, the components of the extraction buffer may have the following ranges of concentrations: from approximately 1 mM to approximately 500 mM Tris or any buffer similar to Tris; approximately 1 mM to approximately 500 mM EDTA; approximately 10 mM to approximately 1.4 M NaCl; approximately 0.5% to approximately 10% PVP40; sufficient HCl or sufficient NaOH to bring the pH to approximately 7 to approximately 9; and approximately 0.05% to approximately 3% β-mercaptoethanol. Of note, the salt concentration after one adds CTAB (infra) should not exceed approximately 400 mM so that the nucleic acids can precipitate out of solution and not co-isolate with polysaccharides. Thus, if the concentration of salt in the extraction buffer is exceeds 800 mM, then the volume of CTAB would also increase in order to reduce the salt concentration to the desired range.

Add approximately 400 μL of the extraction buffer (already containing β-mercaptoethanol) to the tube. Alternatively, one can add β-mercaptoethanol directly to the tube prior to or after adding the extraction buffer.

After the extraction buffer, β-mercaptoethanol, and the solid components are combined, one resuspends the pellet (the solid component) thoroughly by vortexing or gently shaking. Next, one adds approximately 4 μL of 10 M NaOH and approximately 40 μL of 40% TWEEN 20 to the tube to lyse the cells (prokaryotic and eukaryotic) that are present in the tube. In an alternative embodiment, one can use between approximately 0.05% (final concentration) and approximately 10% (final concentration) TWEEN 20, TWEEN 40, TWEEN 60, TWEEN 80, Triton X-100, Nonidet P-40, or any similar non-ionic surfactant; and between approximately 10 mM (final concentration) and approximately 1 M NaOH (final concentration). While one can add NaOH and the non-ionic surfactant to the extraction buffer immediately prior to using the extraction buffer, adding NaOH and non-ionic surfactant after resuspending the solid component in the juice in the extraction buffer provides better results. Lysing cells releases nucleic acids, polysaccharides, lipids, proteins and polar material.

Cap the tube tightly and mix well with a vortex to lyse the cells present in the tube. Incubate the tube at approximately 65° C. for between approximately 30 minutes to approximately 1 hour to thoroughly lyse the cells. Allow the tube to cool at room temperature for approximately 5 minutes. Next, the nucleic acids and polysaccharides are separated from the non-polar material, proteins, and lipids (or the non-polar material, proteins and lipids are separated from the nucleic acids and polysaccharides). This separation step is accomplished by adding approximately 444 μl chloroform:isoamylalcohol (24:1, v/v) or an equivalent amount of chloroform to the tube, vortexing for 10 seconds or between 5 seconds and 5 minutes, and centrifuging at approximately 13,000 rpm (or between approximately 7,000 rpm and approximately 25,000 rpm) for approximately 10 minutes (or between approximately 5 minutes to 2 hours) to separate the aqueous phase (nucleic acids and polysaccharides) from the organic phase (non-polar material and lipids) and from the interface (proteins) (or to separate the organic phase and interface from the aqueous phase). Further separation occurs by transferring the aqueous phase (approximately 300 µL) to a new tube, leaving the organic phase and interface in the original tube. Add approximately 300 µL of pre-warmed 4% hexadecetyl trimethyl ammonium bromide (CTAB) (final concentration: 2%) (or approximately 1:1 volume of the isolated aqueous phase and CTAB) to separate the nucleic acids from the polysaccharides (or the polysaccharides from the nucleic acids). DNA and other nucleic acids are not soluble in the aqueous phase containing CTAB and the salt at a concentration of approximately 400 mM or less. Yet, pectin and other polysaccharides remain soluble in the aqueous phase in the presence of CTAB. If the salt concentration is greater than approximately 800 mM in the extraction buffer, then one should add sufficient quantity of CTAB solution to reduce the final salt concentration to approximately 400 mM or less. Alternatively the final CTAB concentration can range between approximately 0.5% and approximately 5%.

Mix well by inverting the tube between approximately 1 and approximately 100 times. Incubate the tube at approximately 65° C. (or between approximately 60° C. and approximately 80° C.) for approximately 30 minutes (or between approximately 10 minutes and approximately 60 minutes) to help nucleic acids come out of solution from the aqueous phase. Next, centrifuge the tube at approximately 13,000 rpm (or approximately 7,000 rpm to approximately 25,000 rpm) for approximately 15 minutes (or approximately 5 minutes to approximately 1 hour) and discard the supernatant (aqueous phase) containing the polysaccharides, leaving pelletted nucleic acids in the tube. Add approximately 1 ml of 70% ethanol (or approximately 1 ml of between approximately 60% and approximately 100% ethanol, or approximately 1 ml of between approximately 60% and approximately 100% ethanol prepared in TE buffer (10 mM Tris, 1 mM EDTA) or prepared in 10 mM Tris-HCl) to the pellet. Invert the tubes between 1 and approximately 100 times, and allow the tube to remain at room temperature for approximately 10 second to approximately 240 minutes to dissolve and remove excess CTAB. Centrifuge the tube again at approximately 13,000 rpm (or from approximately 7,500 rpm to approximately 25,000 rpm) for approximately 10 minutes (or from approximately 2 minutes to approximately 2 hours) at approximately 20° C. (or between approximately 0° C. to approximately 40° C.) to pellet the nucleic acids and again discard the supernatant.

Re-suspend the pelletted nucleic acids in approximately 500 µL of 1 M NaCl (or alternatively between approximately 50 mM NaCl and approximately 5 M NaCl) and incubate at approximately 65° C. (or between approximately 25° C. and approximately 85° C.) for approximately 5 minutes (or approximately 10 seconds and approximately 240 minutes). Add approximately 400 µL of 2-propanol (concentration can range from between approximately 10% to approximately 100%) to the tube and invert the tube repeatedly for approximately 30 seconds (or between approximately 5 seconds and approximately 240 minutes), then allow to remain up-right at room temperature for approximately 5 minutes (or between approximately 5 seconds and approximately 240 minutes) to precipitate the nucleic acids. Any remaining CTAB dissolves in the alcohol while the nucleic acids precipitate out of solution. Centrifuge the tube at approximately 13,000 rpm (or from approximately 7,500 rpm to approximately 25,000 rpm) for approximately 15 minutes (or from approximately 2 minutes to approximately 2 hours) at 20° C. (or from approximately 0° C. to approximately 50° C.) to pellet the nucleic acids, discard the supernatant and retain the pelletted, isolated nucleic acids. Next add approximately 1 ml of 70% ethanol (concentration can range between approximately 60% to approximately 100%) to the tube, or alternatively add approximately 1 ml of between approximately 60% and approximately 100% ethanol prepared in TE buffer (10 mM Tris, 1 mM EDTA) or prepared in 10 mM Tris-HCl, to the tube to wash the pelletted, isolated nucleic acids again and to remove non-nucleic acid substances. Invert the tube once, twice, three or more times to wash the isolated nucleic acids and remove any remaining salts. Centrifuge the tube again at 13,000 rpm (or from approximately 7,500 rpm to approximately 25,000 rpm) for approximately 10 minutes (or from approximately 2 minutes to approximately 2 hours) at 20° C. (or from approximately 0° C. to approximately 50° C.) and discard the supernatant to remove the liquids from the pelletted, isolated nucleic acids. Air dry the isolated nucleic acid pellet at approximately 30° C. (or from approximately 0° C. to approximately 70° C.) for approximately 30 minutes (or from approximately 2 minutes to approximately 12 hours). Dissolve the nucleic acids in approximately 30 µL of DNA nuclease-free and RNA nuclease-free water or in TE buffer (10 mM Tris and 1 mM EDTA, pH 8) or in 10 mM Tris-HCl, pH between 7.5 and 8.0.

To assist in the practice of the invention's nucleic acid isolation method, another aspect of this invention is a kit containing the extraction buffer in a first container, a second container containing β-mercaptoethanol, which can be added to the extraction buffer prior to use, and instructions for use of the material in the containers. In another embodiment, the kit could also have a third container which holds a mixture of NaOH and a surfactant (non-ionic or cationic surfactant) or these two compounds can be separate containers (thus the kit would have a third and fourth container).

In yet another embodiment, one can have a kit with a plurality of containers that contain, individually or in combination, the components of the extraction buffer, one or two containers to hold NaOH and a surfactant (non-ionic or cationic surfactant) either together or individually, optionally a container to hold CTAB, optionally another container to hold the chloroform or similar compounds, optionally one or more containers to hold the alcohol solutions, and instructions on use of the materials in the kit for isolation of nucleic acids.

Because the inventions described and claimed herein use biotechnology methods, a brief description of some of these methods is provided.

Polymerase chain reaction (or PCR) is a technique to copy (or amplify) a small quantity of nucleic acids. Using PCR, one can generate greater than 100,000,000 or even one billion copies of the desired nucleic acid within a couple of hours. To amplify a segment of DNA using PCR, the sample is first heated so the DNA denatures (separates into two pieces of single-stranded DNA). Next, the sample is cooled to a temperature lower than the melting (or denaturing) temperature of the DNA but still substantially higher than room temperature. At this temperature, Taq polymerase (a DNA polymerase active at high temperatures) synthesizes two new strands of DNA, using the original strands as templates and primers that bind to the original strands of DNA as initiation points for DNA extension by Taq polymerase. Of course, sufficient amounts of free nucleic acids are added to the reaction mixture for use by Taq polymerase to generate the new DNA. This process results in the duplication of a section of the original DNA based on the binding location of the primers. Each new DNA segment (also referred to as an amplicon) contains one old and one new strand of DNA. The sample is heated again to denature the DNA again and allowed to cool so that Taq polymerase can generate new amplicons. The cycle of denaturing and synthesizing new DNA is repeated as many as thirty or forty times, leading to approximately one billion or more amplicons. A thermocycler is a programmable apparatus that automates the temperature changes utilized in PCR, controlling DNA denaturation and synthesis. PCR can be completed in a few hours. Some early U.S. patents on PCR include U.S. Pat. Nos. 4,683,195; 4,683,202; and 4,800,159.

Quantitative PCR (qPCR), also called real-time PCR, involves monitoring DNA amplification during each cycle of PCR using a fluorescent label. When the DNA is in the log linear phase of amplification, the amount of fluorescence increases above the background. The point at which the fluorescence becomes measurable is called the Cycle Threshold (Ct) or crossing point. By using multiple dilutions of a known amount of standard DNA, a standard curve can be generated of log concentration against Ct. The amount of nucleic acids in an unknown sample can then be calculated from its Ct value. For this invention, the higher the Ct value, the smaller the quantity of a microorganism's DNA is present in the assayed liquid. Conversely, the lower the Ct value, the higher the quantity of a microorganism's DNA is present in the assayed liquid. For this invention, as it relates to CLas, Ct value of approximately 35 to approximately 36 or less obtained using Li primers indicates that the citrus tree or trees from which the juice is obtained is infected with CLas. For this invention, as it relates to CLas, a Ct value of approximately 30 to approximately 32 or less using LJ primers indicates that the citrus tree or trees from which the juice is obtained is infected with CLas. For the Li primers (SEQ ID NO: 3 and SEQ ID NO: 4), Ct values between approximately 30 and approximately 35 indicate some decrease in juice quality, but Ct values of approximately 30 and below, indicate very poor juice quality. For the LJ primers (SEQ ID NO: 1 and SEQ ID NO: 2), Ct values between approximately 25 and approximately 30 indicate some decrease in juice quality, but Ct values of approximately 25 and below indicate very poor juice quality.

Two types of fluorescent labels can be used with qPCR. One label is an intercalating dye that incorporates into double-stranded DNA, such as SYBR® Green. An intercalating dye is appropriate when a single amplicon is being studied. The second type of fluorescent label is a probe that binds specifically to the target DNA, such as TaqMan® probes, Molecular Beacons™, or Scorpion primers. The probe is an oligonucleotide with a fluorescent dye (such as Texas Red®, FAM, TET, HEX, TAMRA, JOE, and ROX) and a quencher (such as Dabcyl, Dabsyl, and the minor groove binding nonfluorescent quencher (MGBNFQ)) chemically attached to the oligonucleotide. The oligonucleotide itself has no significant fluorescence, but fluoresces either when annealed to the template (as in Molecular Beacons™) or when the dye is clipped from the oligonucleotide during extension (as in TaqMan® probes). The fluorescent compositions described herein are simply examples of compositions for imaging, identifying, and/or quantifying DNA. Instead of the fluorescent compositions described herein, one can label DNA with compositions that are known in the art (some of which are described infra) or that are developed in the future. These labels can be used to image, identify, and/or quantify DNA using similar methods as described herein. The fluorescent compositions are simply one well-known and well-accepted compositions for imaging, identifying, and/or quantifying DNA for the methods described herein. The oligonucleotide for a probe is at least approximately 8 nucleotides in length. In some embodiments, the oligonucleotide for a probe is between approximately 8 bases and approximately 50 bases long. In other embodiments, the oligonucleotide for a probe is between approximately 15 bases and approximately 45 bases long.

In addition to qPCR, one can use multiplex PCR to quantify the nucleic acids from several different microorganisms simultaneously. Multiplex PCR is similar to qPCR but uses dyes with distinct fluorescent emissions for each probe used during the amplification process. Alternatively, instead of using fluorescent emissions in qPCR or multiplex PCR to determine the quantity of amplified DNA, one can use other methods known in the field to measure the amplified DNA, some of which is described infra. The ranges of Ct values for each primer described above are applicable for multiplex PCR.

The term "nucleic acid" as used herein, refers to a polymer of ribonucleotides or deoxyribonucleotides. Typically, "nucleic acid" polymers occur in either single- or double-stranded form, but are also known to form structures comprising three or more strands. The term "nucleic acid" includes naturally occurring nucleic acid polymers as well as nucleic acids comprising known nucleotide analogs or modified backbone residues or linkages, which are synthetic, naturally occurring, and non-naturally occurring, which have similar binding properties as the reference nucleic acid, and which are metabolized in a manner similar to the reference nucleotides. Exemplary analogs include, without limitation, phosphorothioates, phosphoramidates, methyl phosphonates, chiral-methyl phosphonates, 2-O-methyl ribonucleotides, peptide-nucleic acids (PNAs). "DNA", "RNA", "polynucleotides", "polynucleotide sequence", "oligonucleotide", "nucleotide", "nucleic acid", "nucleic acid molecule", "nucleic acid sequence", "nucleic acid fragment", and "isolated nucleic acid fragment" are used interchangeably herein.

The term "label" as used herein, refers to a composition detectable by spectroscopic, photochemical, biochemical, immunochemical, or chemical means. Exemplary labels include $^{32}P$ (or other isotopes), fluorescent dyes, electron-dense reagents, enzymes (e.g., as commonly used in an ELISA), biotin, digoxigenin, or haptens and proteins for which antisera or monoclonal antibodies are available.

As used herein a nucleic acid "probe", oligonucleotide "probe", or simply a "probe" refers to a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (e.g., 7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. In one exemplary embodiment, probes are directly labeled as with isotopes, chromophores, lumiphores, chromogens etc. In other exemplary embodiments probes are indirectly labeled e.g., with biotin to which a streptavidin complex may later bind. By assaying for the presence or absence of the probe, one can detect the presence or absence of the select sequence or subsequence.

Thus, the term "probe" as used herein refers to a probe that is bound, either covalently, through a linker or a chemical bond, or noncovalently, through ionic, van der Waals, electrostatic, or hydrogen bonds to a label such that the presence of the probe may be detected by detecting the presence of the label bound to the probe.

The term "primer" as used herein, refers to short nucleic acids, typically a DNA oligonucleotide of at least approximately 8 nucleotides in length. In some embodiments, a primer is between approximately 8 bases and approximately 50 bases long. In other embodiments, a primer is between approximately 15 bases and approximately 45 bases long. In an exemplary embodiment, primers are annealed to a complementary target DNA strand by nucleic acid hybridization to form a hybrid between the primer and the target DNA strand. Annealed primers are then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

PCR primer pairs are typically derived from a known sequence, for example, by using computer programs intended for that purpose such as Primer (Version 0.5 ©1991, Whitehead Institute for Biomedical Research, Cambridge, Mass.). One of ordinary skill in the art will appreciate that the specificity of a particular probe or primer increases with its length. Thus, for example, a primer comprising 20 consecutive nucleotides of a promoter complex sequence will anneal to a related target sequence with a higher specificity than a corresponding primer of only 15 nucleotides. Thus, in an exemplary embodiment, greater specificity of a nucleic acid primer or probe is attained with probes and primers selected to comprise 20, 25, 30, 35, 40, 50 or more consecutive nucleotides of a selected sequence.

Nucleic acid probes and primers are readily prepared based on the nucleic acid sequences disclosed herein. Methods for preparing and using probes and primers and for labeling and guidance in the choice of labels appropriate for various purposes are discussed, e.g., in Sambrook et al., *Molecular Cloning, A Laboratory Manual 2nd ed.* 1989, Cold Spring Harbor Laboratory; and *Current Protocols in Molecular Biology*, Ausubel et al., eds., 1994, John Wiley & Sons).

The term "capable of hybridizing under stringent hybridization conditions" as used herein, refers to annealing a first nucleic acid to a second nucleic acid under stringent hybridization conditions (defined below). In an exemplary embodiment, the first nucleic acid is a test sample, and the second nucleic acid is the sense or antisense strand of a nucleic acid of interest. Hybridization of the first and second nucleic acids is conducted under standard stringent conditions, e.g., high temperature and/or low salt content, which tend to disfavor hybridization of dissimilar nucleotide sequences.

Example 1 DNA Isolation from Juice

It is useful to make a stock solution of the extraction buffer. One liter of the extraction buffer contains approximately 12.1 g Tris-base (final concentration: approximately 100 mM), approximately 18.61 g EDTA (final concentration: approximately 50 mM), approximately 29.22 g NaCl (final concentration: approximately 500 mM), approximately 25 g polyvinylpyrrolidone (PVP40) (final concentration: approximately 2.5%), add approximately 800 mL water to dissolve the components. The pH of the extraction buffer is adjusted, if necessary, by adding sufficient 1 M HCl or 1 M NaOH to bring the pH to approximately 8.0. One should add sufficient water to bring the total volume to one liter. Next, one adds approximately 2 µL of β-mercaptoethanol per ml of extraction buffer (the final β-mercaptoethanol concentration is approximately 0.2% (v/v)) to the extraction buffer immediately prior to using the extraction buffer. The salt concentration after one adds CTAB (infra) should not exceed approximately 400 mM so that the nucleic acids can precipitate out of solution and not co-isolate with polysaccharides. Thus, if the concentration of salt in the extraction buffer is exceeds 800 mM, then the volume of CTAB would also increase in order to reduce the salt concentration to the desired range.

Place approximately 0.5 ml orange juice into a 1.5 ml tube and centrifuge at 13,000 rpm for approximately 15 minutes at 20° C. to separate the solid components (plant material and microorganism material) in the juice from the liquid (liquid soluble components). Discard the supernatant and retain the solid components. Add approximately 400 µL of the extraction buffer (already containing β-mercaptoethanol) to the tube. The extraction buffer, especially the β-mercaptoethanol, helps lyse cells (prokaryotic and eukaryotic) present in the solid components present in the juice. The extraction buffer also protects the nucleic acids from degradation.

Resuspend the pellet (the solid components of the juice) thoroughly via vortexing or gently shaking. Next, add approximately 4 µL of 10 M NaOH and approximately 40 µL of 40% TWEEN 20 to the tube to lyse the cells (prokaryotic and eukaryotic) that are present in the tube. Cap the tube tightly and mix well with a vortex to lyse the cells present in the tube. Incubate the tube at approximately 65° C. for between approximately 30 minutes to approximately 1 hour to thoroughly lyse the cells. Allow the tube to cool at room temperature for approximately 5 minutes. Next, add approximately 444 µl chloroform:isoamylalcohol (24:1, v/v). The addition of chloroform:isoamylalcohol denatures proteins and creates an organic phase into which the lipids and non-polar material dissolve, an interface in which the denatured proteins present, and an aqueous solution into which DNA, pectin, and other polar material dissolves. Vortex for 10 seconds, and centrifuge at 13,000 rpm for approximately 10 minutes to separate the aqueous phase (extraction buffer, NaOH, and non-ionic surfactant) containing DNA and pectin/polysaccharides from the organic phase (chloroform:isoamylalcohol) containing lipids and non-polar material, the interface containing denatured proteins. Transfer the aqueous phase (approximately 300 µL) to a new tube and leave the organic phase and interface in the original tube.

Add approximately 300 µL of pre-warmed 4% hexadecetyl trimethyl ammonium bromide (CTAB) (final concentration: 2%). DNA and other nucleic acids are not soluble in the aqueous phase containing CTAB and the salt at a concentration of approximately 400 mM or less. Yet, pectin and other polysaccharides remain soluble in the aqueous phase in the presence of CTAB. Thus, this step allows one to separate nucleic acids and polysaccharides. Mix well by inverting the tube several times and incubate at 65° C. for approximately 30 minutes to help nucleic acids come out of solution from the aqueous phase. Next, centrifuge the tube at 13,000 rpm for approximately 15 minutes and discard the supernatant (aqueous phase) containing the polysaccharides, leaving pelletted nucleic acids in the tube. Add approximately 1 ml of 70% ethanol to the pellet. Invert the tubes twice and allow the tube to remain at room temperature for approximately one to approximately two minutes to dissolve and remove excess CTAB. Centrifuge the tube again at 13,000 rpm for approximately 10 minutes at 20° C. to pellet the nucleic acids and again discard the supernatant. Resuspend the pelletted nucleic acids in approximately 500 µL of 1 M NaCl, and incubate at 65° C. for approximately 5 minutes. Add approximately 400 µL of 2-propanol to the tube and invert the tube repeatedly for approximately 30 seconds, then allow to remain up-right at room temperature for approximately 5 minutes. Any remaining CTAB dissolves in the alcohol while the nucleic acids precipitate out of solution. Centrifuge the tube at 13,000 rpm for approximately 15 minutes at 20° C. to pellet the nucleic acids, discard the supernatant and retain the pelletted, isolated nucleic acids. Next add approximately 1 ml of 70% ethanol to the tube to the tube to wash the pelletted, isolated nucleic acids. Invert the tube once, twice, three or more times to wash the isolated nucleic acids and remove any remaining salts. Centrifuge the tube again at 13,000 rpm for approximately 10 minutes at 20° C. and discard the supernatant to remove the liquids from the pelletted, isolated nucleic acids. Air dry the isolated nucleic acid pellet at 30° C. for approximately 30 minutes. Dissolve the nucleic acids in 30 µL of DNA nuclease-free and RNA nuclease-free water or in TE buffer (10 mM Tris and 1 mM EDTA, pH 8) or in 10 mM Tris-HCl, pH between 7.5 and 8.0.

Of the two categories of DNA isolation and purification methods discussed supra, the protocol described herein uses CTAB but not SDS and KoAC, so it belongs to the CTAB category. The present invention differs from the published CTAB DNA extraction method (Allen, et al., (2006)) as follows: 1) Using NaOH and Tween 20 (or similar compositions) to help lyse the cells, resulting in an increased DNA yield. 2) PVP40 is in the Extraction Buffer to absorb polyphenols present in the juice and lysed cells, resulting in cleaner DNA. 3) CTAB precipitates and separates DNA from the extraction buffer, prior to using any alcohol (including isopropanol) to precipitate DNA. This step efficiently removes polysaccharides (including pectin) and dramatically improves the DNA A260/A230 ratio (>2.2), indicating that the DNA is free from polysaccharide contamination. 4) The NaCl concentration in the Extraction Buffer can range from approximately 10 mM to approximately 800 mM, in some embodiments, which is less than the NaCl concentration in the prior art methods (however the concentration can range up to 1.4 M on the condition that one accordingly increases the volume of CTAB added in order to bring the final salt concentration to approximately 400 mM or less). 5) CTAB is not in extraction buffer, but is used during at a later step (after removal of proteins and other polar material via addition of chloroform to create an organic phase) to separate DNA from polysaccharides. Nucleic acids are not soluble in an aqueous solution containing CTAB when the NaCl concentration in the aqueous solution is approximately 400 mM or less. Thus, in one embodiment, the salt concentration in the extraction buffer is approximately 500 mM so that after separation of the organic phase (containing lipids and non-polar components dissolved in chloroform) and the interface (containing denatured proteins) from the aqueous phase (containing nucleic acids and polysaccharides) (alternatively, the aqueous phase is separated from the interface and the organic phase), and upon addition of the CTAB solution to the aqueous phase, the salt concentration is approximately 250 mM.

This DNA isolation and purification method produces highly purified DNA (A260/A280=2.02±0.03, which means the DNA is free of protein contamination; and A260/A230=2.29±0.05, which means the DNA is free of polysaccharide, salts or solvents contamination) with high yield (approximately 10 µg DNA per 0.5 ml of orange juice). See FIG. 1 which illustrates the purity of DNA as measured by a Nano-Drop spectrophotometer (ThermoFisher Scientific, Waltham, Mass.). Further, the cost for performing this DNA isolation and purification method is extremely low (less than $0.10/sample). Table 1 contains information about the DNA yield and purity of the novel method of this invention, some prior art methods, and several other methods that were used but did not generate results comparable to this method described herein.

TABLE 1

| DNA Isolation & Purification Method | DNA yield (µg/0.5 ml juice) | A260/A280 | A260/A230 |
| --- | --- | --- | --- |
| Protocol described in Experiment 1 | 10.02 ± 1.50 | 2.02 ± 0.03 | 2.29 ± 0.05 |
| CTAB method (Allen, et al., Nat. Protoc., 1(5): 2320-2325 (2006)) | 4.39 ± 1.15 | 1.95 ± 0.11 | 1.16 ± 0.15 |
| SDS-KoAC method (Dellaporta, et al., Plant Molecular Biology Reporter, 1(4): 19-21(1983)) | 3.71 ± 1.23 | 1.88 ± 0.09 | 0.65 ± 0.11 |
| Combined kits method (Bai, et al., J. Agric. Food Chem. In press (2013)) | 0.58 ± 0.06 | 1.94 ± 0.12 | 1.62 ± 0.10 |
| Bio Sprint 96 DNA plant kit (Qiagen, Cat# 941557 (Germantown, MD)) | 3.55 ± 2.58 | 1.29 ± 0.15 | 0.30 ± 0.08 |
| Protocol described in Experiment 1 except used SDS instead of Tween 20 | no DNA extracted | N/A | N/A |
| CTAB protocol (above) modified by adding PVP, NaOH and Tween 20 to the extraction buffer | 6.85 ± 1.21 | 1.96 ± 0.15 | 1.25 ± 0.07 |

Example 2 CLas DNA Detection

To detect CLas DNA in orange juice obtained from two major orange varieties (Hamlin and Valencia), DNA from the orange juice is isolated and purified using the protocol described in Example 1. Hamlin oranges are obtained from three different healthy trees (one tree received no foliar nutritional spray treatment (U); one tree received a wettable powder nutritional treatment ("WP"); and one tree received a nutritional treatment K ("K")) and five different trees exhibiting HLB disease (one infected tree receiving no foliar nutritional spray treatment ("U"); one infected tree that received the wettable powder nutritional treatment ("WP"); one infected tree that received the nutritional treatment K ("K"); mildly (as defined below in Table 5) infected tree that received the nutritional treatment K ("K"); and severely (as defined in Table 5 below) infected tree that received the nutritional treatment K ("K")).

Valencia oranges are obtained from three different healthy trees (one that received no foliar nutritional spray treatment (U); one that received nutritional treatment MB ("MB"); and one that received nutritional treatment K("K")). The oranges used are either HLB asymptomatic or HLB symptomatic. Thus, asymptomatic oranges and symptomatic oranges are obtained from trees that received no foliar nutritional spray treatment (U); asymptomatic oranges and symptomatic oranges are obtained from trees that received MB nutritional treatment ("MB"); and asymptomatic oranges and symptomatic oranges are obtained from trees that received the nutritional treatment K ("K")).

Juice samples from each type of tree/fruit are obtained by squeezing, separately, the oranges from each type of tree. DNA is isolated and purified from each juice sample using the protocol described in Example 1 above and resuspended in 30 µl of DNA nuclease-free and RNA nuclease-free water. However, any DNA isolation protocol could be used.

After isolating and purifying DNA from each juice sample, qPCR is performed. The primers and probe listed in Table 2 are used in the qPCR of this experiment. The LJ primers which target CLas and CLam hyv$_1$ are described in Morgan, et al., *Mol. and Cell. Probes*, 26:90-98 (2012) and are synthesized by Integrated DNA Technologies, Inc. (Coralville, Iowa). The LJ primer working solution contains 10 µM LJ-F and 10 µM LJ-R. The Li primers (HLBas (F) and HLBr (R)) which target CLas 16S rDNA are described in Li, et al., *J. of Microbiol. Methods*, 66:104-115 (2006) and are synthesized by Applied Biosystems, Inc. (Carlsbad, Calif.). The Li primer working solution contains 5 µM HLBas (F) and 5 µM HLBr (R). The Li probe working solution that is used with the Li primers contains 5 µM HLBp (probe).

TABLE 2

| Primer/ Probe Name | Sequence |
|---|---|
| LJ-F | 5'-GCCGTTTTAACACAAAAGATGAATATC-3' (SEQ ID NO: 1) |
| LJ-R | 5'-ATAAATCAATTTGTTCTAGTTTACGAC-3' (SEQ ID NO: 2) |
| HLBas (F) | 5'-TCGAGCGCGTATGCAATACG-3' (SEQ ID NO: 3) |
| HLBr (R) | 5'-GCGTTATCCCGTAGAAAAAGGTAG-3' (SEQ ID NO: 4) |
| HLBp (probe) | 6-FAM-AGACGGGTGAGTAACGCG-TAMRA (or-MGBNFQ) (SEQ ID NO: 5) |

6-FAM = 6-carboxyfluorescein
TAMRA = carboxytetramethylrhodamine
MGBNFQ = the minor groove binding nonfluorescent quencher For each qPCR reaction, 2 µL of each isolated and purified DNA samples obtained from each orange juice sample are used per 15 µL reaction. For qPCR reactions using LJ primers, each 15 µL reaction contains 4.75 µL of DNA/RNA nuclease-free water, 0.75 µL of LJ primer working solution, 7.5 µL of SYBR® Green PCR Master Mix (Applied Biosystems, Inc., Carlsbad, Calif.) and 2 µL of isolated and purified DNA (obtained from one orange juice sample). For qPCR reactions using Li primers, each 15 µL reaction contains 4.3 µL of DNA/RNA nuclease-free water, 0.75 µL of Li primer working solution, 0.45 µL of Li probe working solution, 7.5 µL of TaqMan® Universal Master Mix (Applied Biosystems, Inc., Carlsbad, Calif.) and 2 µL of isolated and purified DNA (obtained from one orange juice sample). See Table 3 infra.

To make the reaction mixture for all samples, the total reaction number needs to be calculated based on the DNA sample number, the replications for each DNA sample (usually triplicate for each DNA sample, at least duplicate), positive control, negative control (no template control ("NTC")), etc. Plus it is helpful, but not necessary, for one to increase the total reaction number slightly (such as by two, three, or four; or such as by one for every ten samples to be performed) in order to have sufficient amount of reagents for the assays. The number of µL for each component (except DNA) is added to the reaction mixture based on the number of qPCR reactions to be performed and the volume of each component for one qPCR reaction ((qPCR reaction number)×(number of µL per reaction for each component as described above)=number of µL of each component). After assembling all the components together (excluding the DNA), mix well gently (for example, by gently pipetting up and down several times) and spin down briefly. Aliquot the reaction mixture into a 96-well PCR reaction plate, 13 µL per well; and then add 2 µL of DNA to each well (for NTC, add 2 µL of water). Seal the plate with an optical adhesive film, and spin the plate in a mini plate spinner for approximately 1 minute. The qPCR reaction reagents and quantities for each LJ primer 15 µL reaction and for each Li primer 15 µL reaction are summarized in Table 3 below.

TABLE 3

| | 1 Rx (µL) |
|---|---|
| LJ primer 15 µL reaction: | |
| SYBR® Green PCR Master Mix | 7.5 |
| LJ primer set (LJ-F and LJ-R, 10 µM each) | 0.75 |
| Water | 4.75 |
| Isolated and purified DNA (from orange juice) | 2 |
| Li primer 15 µL reaction: | |
| TaqMan® Universal Master Mix II, no UNG | 7.5 |
| Li primer set (HLBas (F) and HLBr (R), 5 µM each) | 0.75 |
| Probe (HLBp) | 0.45 |
| Water | 4.3 |
| Isolated and purified DNA (from orange juice) | 2 |

7500 Real-Time PCR system (Applied Biosystems, Inc., Carlsbad, Calif.) is used for the qPCR reaction. The qPCR parameters are as follows: 95° C. for 10 minutes, followed by 40 cycles at 95° C. for 15 seconds, and 60° C. for 1 minute, with fluorescence signal capture at each stage of 60° C. For the SYBR® Green Real-Time PCR reaction (for LJ primers), the default Melt Curve (disassociation) stage is continued after the 40 cycles of PCR reaction. Cycle threshold (Ct) values are analyzed using ABI 7500 Software version 2.0.6 (Applied Biosystems, Inc., Carlsbad, Calif.)) with a manually set threshold at 0.02 and automated baseline settings. The qPCR parameters are summarized in Table 4, infra. If performing the SYBR® Green reaction (for LJ primers), continue to the default Melt Curve (disassociation) stage after the 40 cycles of PCR reaction. The Li primers generate an amplicon of 70 bp (Li, et al. 2006)). The LJ primers generate an amplicon of 100 bp (Morgan, et al. (2012)).

TABLE 4

| Cycles | 1 | 40 | |
|---|---|---|---|
| Temp (° C.) | 95 | 95 | 60 |
| Time | 10 minutes | 15 seconds | 1 minute (collect data) |

The Ct values for the isolated and purified DNA obtained from juice obtained from each type of Hamlin orange tree and from each type of Valencia orange tree are shown in Table 5, infra. In qPCR using Li primers, Ct value of 36 or less is the considered by USDA as indicative of the citrus tree being infected with CLas (see Li, et al., (2006)), however the Ct value of 35 or less is used for this example. In the qPCR using LJ primers, USDA has not determined a Ct value that is indicative of a citrus tree being infected with CLas. For the purposes of this invention, a Ct value of approximately 30 to approximately 31 or less is considered indicative of the citrus tree being infected with CLas.

TABLE 5

| Sample ID | Li primer (16S rDNA) $C_T$ | LJ primer (prophage) $C_T$ |
|---|---|---|
| Hamlin orange juice | | |
| U-healthy | ND | ND |
| WP-healthy | ND | ND |
| K-healthy | 36.1 ± 0.1 | 30.5 ± 0.1 |
| U-HLB | 29.7 ± 0.2 | 26.8 ± 0.1 |
| WP-HLB | 34.3 ± 0.08 | 27.8 ± 0.5 |
| K-HLB | 31.2 ± 0.1 | 28.4 ± 0.5 |
| K-HLB mild | 35.5 ± 0.7 | 30.4 ± 0.3 |
| K-HLB severe | 29.5 ± 0.1 | 26.7 ± 0.1 |
| Valencia orange juice | | |
| U Healthy | 35.8 ± 0.4 | 32.8 ± 0.3 |
| U Asymp (HLB) | 33.4 ± 0.5 | 29.6 ± 0.2 |
| U Symp (HLB) | 32.8 ± 0.2 | 27.5 ± 0.2 |
| MB Healthy | 34.9 ± 0.1 | 30.2 ± 0.4 |
| MB Asymp (HLB) | 34.1 ± 0.3 | 29.1 ± 0.4 |
| MB Symp (HLB) | 32.3 ± 0.3 | 27.7 ± 0.8 |
| K Healthy | 34.1 ± 1.0 | 29.5 ± 0.7 |
| K Asymp (HLB) | 33.0 ± 0.5 | 27.7 ± 0.02 |
| K Symp (HLB) | 30.7 ± 0.1 | 26.0 ± 0.1 |

ND: No amplification detected
U: no foliar nutritional spray treatment; WP: a wettable powder nutritional treatment; MB: nutritional treatment MB; K: nutritional treatment K; Mild: trees rated as 2 on scale of 4 where 4 represents most symptomatic infected trees; Severe: trees rated as 3 or 4.
Asymp: juice from HLB asymptomatic fruits; Symp: juice from HLB symptomatic fruits.

The foliar nutritional spray treatments (WP, K and MB) are known in the art field treatments that growers are using to mitigate the effects of HLB disease on the deterioration of infected trees. The oranges obtained from "healthy" trees are trees that were initially considered healthy because the trees were not symptomatic for HLB. However, based on the data obtained, some of the "healthy" trees are infected with CLas. See Ct value for MB Healthy and K Healthy in Table 5 above. Even the trees indicated as "U Healthy" had a Ct value that is borderline (if one uses Ct 36 as the cut-off value) and thus are probably infected with CLas.

Example 3 Detection of CLas DNA in Commercial Orange Juice

Five brands of juice are purchased at a local store: Orange juice 1, Orange juice 2, Orange juice 3, Orange juice 4, and Orange juice 5. DNA isolation and purification is performed as described in Example 1 for each brand of juice. Next, qPCR is performed as described in Example 2 supra on each isolated and purified DNA obtained from each juice brand using Li primers and LJ primers. Ct value is determined for each sample, in triplicate. The results are in Table 6.

TABLE 6

| Juice Brand | Li primers (16S rDNA) $C_T$ | LJ primer (hyv$_1$) $C_T$ |
|---|---|---|
| Orange juice 1 | 30.6 | 30.2 |
| Orange juice 1 | 30.6 | 30.8 |
| Orange juice 1 | 30.8 | 31.0 |
| Orange juice 2 | 31.6 | 30.0 |
| Orange juice 2 | 31.9 | 30.1 |
| Orange juice 2 | 31.6 | 30.3 |
| Orange juice 3 | 31.6 | 28.5 |
| Orange juice 3 | 32.2 | 29.2 |
| Orange juice 3 | 31.8 | 28.7 |
| Orange juice 4 | 30.9 | 26.9 |
| Orange juice 4 | 30.6 | 27.0 |
| Orange juice 4 | 30.8 | 26.7 |
| Orange juice 5 | 32.1 | 30.9 |
| Orange juice 5 | 32.9 | 30.4 |
| Orange juice 5 | 32.0 | 31.1 |

Ct is cycle value using two primers. As discussed supra, any Ct value under 35 using Li primers indicates that the citrus trees from which a majority of the juice is obtain are infected with CLas and any Ct value under 31 using LJ primers indicates that the citrus trees from which a majority of the juice is obtained are infected with CLas.

Example 4 Quality Control Assay to Predict Juice Flavor Quality

This experiment is performed to determine if the HLB off-flavor of orange juice (as assessed by ten to twelve people trained for descriptive sensory analysis) can be determined by the Ct values obtained by qPCR of isolated and purified DNA for CLas (one of the causal organism for HLB disease) from orange juice. The ten to twelve people are trained to evaluate samples of orange juice and determine the flavor of the juice. Orange juice samples are obtained from 53 HLB-affected groups of oranges (~400-500 fruit per group) of different varieties and harvest dates, from oranges from healthy or infected trees (some trees had received nutritional treatments) that were symptomatic (fruit were small green or lopsided) or asymptomatic for the disease to get a wide range of orange juice flavor quality. DNA from the juice samples is isolated and purified using the protocol of Example 1. qPCR is performed, and Ct values obtained, on the isolated and purified DNA using the Li primers and LJ primers per the methods of Example 2. Flavor rating of flavor descriptors (orange, grapefruit, fruity-non-citrus, orange peel, green, stale, oxidized oil and typical HLB off-flavor), taste descriptors (sweetness, sourness, umami, bitterness and metallic), mouth feel descriptors (body, tingling, astringent, burning) and aftertaste descriptors (bitter, astringent burning) is on a scale of 0 to 15, where 15 is the highest intensity rating of a descriptor. The data is presented in Tables 7, 8, 9, 10 and 11 below.

For Tables 7, 8, 9, 10 and 11, Hamlin or Valencia oranges harvested in December, January or April (as indicated) of different years are obtained from healthy trees (receiving no foliar nutritional spray treatment (U); receiving a wettable powder nutritional treatment WP ("WP"); and receiving nutritional treatment KP ("KP")), and trees exhibiting HLB disease (receiving no foliar nutritional spray treatment (U); receiving a wettable powder nutritional treatment WP ("WP"); receiving nutritional treatment KP ("KP"); and mildly infected trees (MILD: trees receiving nutritional treatment KP ("KP"), rated as 2 on scale of 4 where 4 represents most symptomatic infected trees)). Some samples are juice blends of healthy and HLB fruit, as indicated in the tables.

TABLE 7

Flavor descriptors

| Sample | Orange | Grapefruit | Fruity-non-citrus | Orange peel | Green | Stale | Oxidized oil | Typical HLB |
|---|---|---|---|---|---|---|---|---|
| Hamlin December Healthy | 5.2 | 2.2 | 1.6 | 2.6 | 1.6 | 1.5 | 1.1 | 2.4 |
| Hamlin Decmber HLBa | 2.5 | 6.3 | 0.4 | 3.5 | 2.3 | 3.1 | 3.5 | 7.7 |
| Hamlin December HLBs | 2.2 | 6.7 | 0.3 | 4.8 | 3.0 | 3.6 | 3.9 | 8.8 |
| Hamlin January Healthy | 4.8 | 1.3 | 2.8 | 2.0 | 2.1 | 3.1 | 2.2 | 3.4 |
| Hamlin January HLBa | 3.7 | 2.0 | 1.3 | 2.3 | 2.3 | 2.7 | 2.0 | 4.0 |
| Hamlin January HLBs | 3.1 | 3.0 | 1.3 | 2.9 | 2.3 | 3.3 | 2.5 | 5.9 |
| Valencia April Healthy | 5.8 | 1.5 | 2.6 | 2.8 | 1.5 | 1.0 | 1.0 | 1.9 |
| Valencia April HLBa | 6.3 | 1.4 | 2.1 | 2.7 | 1.5 | 0.9 | 1.0 | 1.7 |
| Valencia April HLBs | 5.3 | 2.1 | 2.1 | 2.9 | 1.5 | 1.3 | 1.2 | 2.9 |
| Hamlin April U-Healthy | 3.6 | 1.6 | 2.0 | 1.4 | 2.4 | 2.4 | 1.3 | 3.2 |
| Hamlin January U-HLBa | 2.9 | 2.4 | 1.4 | 2.4 | 2.0 | 3.1 | 2.0 | 5.0 |
| Hamlin January U-HBLs | 2.8 | 2.5 | 1.2 | 2.3 | 2.5 | 4.0 | 2.5 | 5.8 |
| Hamlin January KP-Healthy | 3.5 | 1.8 | 1.8 | 2.1 | 2.0 | 3.1 | 2.2 | 3.7 |
| Hamlin January KP-HLBs | 3.8 | 2.0 | 1.9 | 1.9 | 2.0 | 2.8 | 2.0 | 3.7 |
| Hamlin January WP-Healthy | 3.1 | 2.0 | 1.1 | 2.1 | 2.1 | 2.6 | 1.5 | 4.2 |
| Hamlin January WP-HLBa | 2.5 | 2.2 | 0.8 | 2.0 | 2.3 | 2.7 | 1.4 | 4.5 |
| Hamlin January WP-HLBs | 3.1 | 2.1 | 0.9 | 2.2 | 2.4 | 2.8 | 1.7 | 4.9 |
| Valencia April U-Healthy | 6.2 | 1.2 | 3.1 | 2.1 | 1.5 | 0.9 | 1.0 | 1.2 |
| Valencia April U-HLBa | 5.6 | 1.2 | 2.7 | 2.2 | 1.3 | 1.1 | 1.3 | 1.6 |
| Valencia April U-HLBs | 6.4 | 1.2 | 3.3 | 2.6 | 1.5 | 0.3 | 0.5 | 0.9 |
| Valencia April KP-Healthy | 6.6 | 1.1 | 2.7 | 2.7 | 1.3 | 1.2 | 1.0 | 1.7 |
| Valencia April KP-HLBa | 6.5 | 1.0 | 3.3 | 2.7 | 1.1 | 1.3 | 1.2 | 1.7 |
| Valencia April KP-HLBs | 5.5 | 2.5 | 1.8 | 3.4 | 1.9 | 1.8 | 1.3 | 3.4 |
| Valencia April MB-Healthy | 7.2 | 0.7 | 3.2 | 2.3 | 1.6 | 0.7 | 0.5 | 1.1 |
| Valencia April MB-HLBa | 6.0 | 1.0 | 3.3 | 1.9 | 1.3 | 1.4 | 1.0 | 1.5 |
| Valencia April MB-HLBs | 5.8 | 1.7 | 2.2 | 2.7 | 1.7 | 1.5 | 1.5 | 2.4 |
| Hamlin U-Healthy | 5.0 | 1.5 | 1.9 | 2.0 | 1.5 | 1.8 | 1.0 | 2.4 |
| Hamlin U-HLB | 3.5 | 2.0 | 1.3 | 2.0 | 2.2 | 2.8 | 2.3 | 4.2 |
| Hamlin KP-HLB Mild | 3.6 | 2.3 | 1.0 | 2.7 | 2.5 | 2.5 | 1.9 | 4.0 |
| Valencia Healthy | 6.3 | 1.2 | 2.4 | 2.2 | 1.5 | 1.2 | 1.0 | 1.7 |
| Valencia HLBa | 5.7 | 1.5 | 2.1 | 2.7 | 2.0 | 1.3 | 1.2 | 2.0 |
| Valencia HLBs | 6.0 | 1.8 | 2.3 | 2.7 | 2.1 | 1.5 | 1.3 | 2.2 |
| Hamlin WP-Healthy | 4.1 | 1.7 | 1.8 | 1.8 | 2.0 | 1.9 | 1.3 | 3.1 |
| Hamlin WP-HLB | 4.0 | 1.5 | 1.6 | 1.8 | 2.2 | 2.3 | 1.4 | 3.2 |
| Valencia Blend 25% Healthy/ 75% HLB | 4.8 | 2.2 | 1.5 | 3.0 | 1.9 | 1.9 | 1.4 | 2.7 |
| Valencia Blend 75% Healthy/ 25% HLB | 5.0 | 2.8 | 1.6 | 2.7 | 2.0 | 1.8 | 1.4 | 2.7 |
| Valencia MB-Healthy | 5.8 | 1.5 | 1.8 | 2.5 | 1.4 | 1.5 | 1.0 | 1.7 |
| Valencia MB-HLB | 5.4 | 2.3 | 1.6 | 3.1 | 1.8 | 1.3 | 1.3 | 2.5 |
| Hamlin Blend 67% healthy/33% HLB | 4.5 | 1.7 | 1.5 | 2.4 | 2.0 | 2.2 | 1.4 | 3.3 |
| Hamlin KP-Healthy | 4.8 | 1.0 | 2.2 | 1.9 | 1.8 | 1.9 | 1.3 | 2.2 |
| Hamlin KP-HLB | 3.6 | 1.8 | 1.0 | 2.1 | 2.0 | 2.7 | 1.5 | 4.2 |
| Hamlin KP-Healthy | 4.8 | 1.4 | 2.2 | 2.0 | 1.5 | 1.6 | 1.2 | 1.8 |
| Hamlin KP-HLB | 3.8 | 1.8 | 1.0 | 2.2 | 2.0 | 1.9 | 1.4 | 4.0 |
| Hamlin KP-HLB Severe | 3.2 | 2.5 | 0.6 | 2.8 | 2.5 | 2.5 | 2.0 | 4.8 |
| Hamlin U-Healthy | 4.4 | 1.4 | 1.7 | 1.7 | 2.3 | 2.6 | 1.2 | 3.3 |
| Hamlin U-HLB | 4.1 | 1.8 | 1.5 | 2.1 | 2.3 | 2.4 | 1.6 | 3.3 |
| Hamlin KP-HLB mild | 3.7 | 1.7 | 1.3 | 2.0 | 2.4 | 2.8 | 1.4 | 4.5 |
| Valencia Blend 50% Healthy/ 50% HLB | 4.9 | 2.5 | 1.3 | 2.6 | 2.0 | 2.3 | 1.8 | 3.9 |
| Valencia U-Healthy | 5.0 | 2.5 | 1.6 | 2.3 | 1.9 | 1.6 | 1.5 | 3.5 |
| Valencia U-HLB | 4.5 | 2.7 | 1.4 | 2.4 | 2.1 | 1.8 | 1.4 | 3.5 |
| Hamlin KP-HLB Severe | 3.4 | 1.8 | 1.0 | 2.0 | 2.3 | 2.4 | 1.5 | 4.7 |
| Hamlin WP-Healthy | 4.3 | 1.6 | 1.1 | 2.0 | 2.0 | 2.1 | 1.7 | 3.4 |
| Hamlin WP-HLB | 3.5 | 1.6 | 0.9 | 2.0 | 2.0 | 2.4 | 1.9 | 4.6 |

TABLE 8

Taste descriptors

| Sample | Sweetness | Sourness | Umami | Bitterness | Metallic |
|---|---|---|---|---|---|
| Hamlin December Healthy | 5.5 | 4.8 | 1.0 | 2.0 | 1.9 |
| Hamlin Decmber HLBa | 3.7 | 5.3 | 2.4 | 6.0 | 3.8 |
| Hamlin December HLBs | 2.8 | 6.2 | 2.8 | 6.6 | 4.9 |
| Hamlin January Healthy | 6.8 | 4.1 | 1.4 | 1.4 | 1.7 |
| Hamlin January HLBa | 5.2 | 4.1 | 1.8 | 2.4 | 2.2 |
| Hamlin January HLBs | 4.8 | 4.5 | 2.4 | 3.5 | 3.1 |

TABLE 8-continued

Table 8

| Sample | Sweetness | Sourness | Umami | Bitterness | Metallic |
|---|---|---|---|---|---|
| Valencia April Healthy | 6.0 | 6.1 | 1.3 | 2.0 | 1.8 |
| Valencia april HLBa | 6.1 | 6.4 | 1.3 | 2.0 | 1.5 |
| Valencia April HLBs | 5.7 | 7.2 | 1.3 | 2.3 | 2.2 |
| Hamlin April U-Healthy | 5.2 | 3.5 | 1.7 | 1.5 | 1.8 |
| Hamlin January U-HLBa | 4.2 | 3.6 | 1.9 | 3.6 | 2.3 |
| Hamlin January U-HBLs | 4.0 | 3.8 | 1.9 | 3.2 | 2.2 |
| Hamlin January KP-Healthy | 4.9 | 3.3 | 1.4 | 2.1 | 2.0 |
| Hamlin January KP-HLBs | 5.6 | 3.6 | 1.8 | 2.0 | 2.0 |
| Hamlin January WP-Healthy | 4.0 | 3.6 | 1.5 | 2.3 | 2.1 |
| Hamlin January WP-HLBa | 3.6 | 3.5 | 1.6 | 3.0 | 2.2 |
| Hamlin January WP-HLBs | 4.1 | 3.7 | 2.0 | 2.1 | 2.2 |
| Valencia April U-Healthy | 6.3 | 5.1 | 0.6 | 1.7 | 1.2 |
| Valencia April U-HLBa | 6.4 | 5.5 | 0.8 | 1.7 | 1.3 |
| Valencia April U-HLBs | 6.5 | 5.8 | 0.9 | 1.8 | 0.9 |
| Valencia April KP-Healthy | 7.2 | 6.0 | 0.9 | 1.9 | 1.7 |
| Valencia April KP-HLBa | 6.9 | 5.8 | 0.9 | 1.9 | 1.8 |
| Valencia April KP-HLBs | 6.0 | 7.3 | 1.4 | 2.4 | 2.8 |
| Valencia April MB-Healthy | 7.7 | 5.0 | 0.5 | 1.5 | 0.8 |
| Valencia April MB-HLBa | 7.0 | 5.0 | 0.8 | 1.6 | 1.5 |
| Valencia April MB-HLBs | 6.4 | 5.8 | 1.3 | 2.2 | 2.2 |
| Hamlin U-Healthy | 5.7 | 4.2 | 1.2 | 1.4 | 1.2 |
| Hamlin U-HLB | 4.4 | 4.0 | 1.8 | 2.8 | 2.2 |
| Hamlin KP-HLB Mild | 4.2 | 4.3 | 1.4 | 2.3 | 1.9 |
| Valencia Healthy | 6.5 | 4.9 | 1.0 | 1.9 | 1.5 |
| Valencia HLBa | 5.6 | 5.8 | 1.4 | 2.2 | 1.8 |
| Valencia HLBs | 5.9 | 6.2 | 1.9 | 2.9 | 2.4 |
| Hamlin WP-Healthy | 5.7 | 4.5 | 1.5 | 2.0 | 1.1 |
| Hamlin WP-HLB | 5.1 | 4.3 | 1.7 | 2.2 | 1.3 |
| Vaencia Blend 25% Healthy/75% HLB | 4.9 | 7.3 | 1.4 | 3.1 | 2.1 |
| Valencia Blend 75% Healthy/25% HLB | 5.0 | 6.8 | 1.3 | 2.8 | 2.0 |
| Valencia MB-Healthy | 6.0 | 6.7 | 1.1 | 2.1 | 1.8 |
| Valencia MB-HLB | 5.8 | 7.4 | 1.0 | 2.6 | 1.7 |
| Hamlin Blend 67% healthy/33% HLB | 5.3 | 4.4 | 1.8 | 2.3 | 1.3 |
| Hamlin KP-Healthy | 6.2 | 3.9 | 1.2 | 1.8 | 1.0 |
| Hamlin KP-HLB | 4.5 | 3.9 | 1.7 | 3.1 | 2.0 |
| Hamlin KP-Healthy | 5.9 | 4.3 | 1.4 | 1.8 | 0.8 |
| Hamlin KP-HLB | 4.1 | 4.4 | 1.5 | 3.3 | 1.8 |
| Hamlin KP-HLB Severe | 4.1 | 4.3 | 2.3 | 3.2 | 1.9 |
| Hamlin U-Healthy | 6.1 | 4.1 | 1.6 | 2.0 | 1.5 |
| Hamlin U-HLB | 5.4 | 4.2 | 1.7 | 2.8 | 1.9 |
| Hamlin KP-HLB mild | 5.0 | 4.1 | 1.7 | 3.1 | 1.6 |
| Valencia Blend 50% Healthy/50% HLB | 4.4 | 7.3 | 1.7 | 3.0 | 2.5 |
| Valencia U-Healthy | 5.1 | 6.8 | 1.3 | 2.4 | 1.8 |
| Valencia U-HLB | 4.4 | 7.5 | 1.5 | 2.8 | 2.2 |
| Hamlin KP-HLB Severe | 4.4 | 4.3 | 1.9 | 3.6 | 1.9 |
| Hamlin WP-Healthy | 5.3 | 4.0 | 1.5 | 2.5 | 1.0 |
| Hamlin WP-HLB | 4.7 | 3.8 | 1.6 | 3.3 | 1.5 |

TABLE 9

Table 9

| Sample | Body | Tingling | Astringent | Burning |
|---|---|---|---|---|
| | | Mouthfeel descriptors | | |
| Hamlin December Healthy | 4.8 | 1.8 | 1.7 | 2.1 |
| Hamlin December HLBa | 4.4 | 3.2 | 2.9 | 3.3 |
| Hamlin December HLBs | 4.3 | 3.2 | 3.8 | 3.2 |
| Hamlin January Healthy | 5.6 | 1.0 | 1.0 | 1.5 |
| Hamlin January HLBa | 5.1 | 1.4 | 1.6 | 1.4 |
| Hamlin January HLBs | 5.2 | 2.0 | 2.5 | 2.2 |
| Valencia April Healthy | 5.9 | 1.9 | 1.6 | 2.4 |
| Valencia april HLBa | 6.1 | 1.6 | 1.7 | 2.5 |
| Valencia April HLBs | 6.1 | 2.6 | 2.3 | 3.3 |
| Hamlin April U-Healthy | 4.5 | 1.0 | 1.3 | 1.3 |
| Hamlin January U-HLBa | 4.5 | 1.4 | 1.8 | 1.8 |
| Hamlin January U-HBLs | 4.1 | 1.8 | 1.9 | 1.8 |
| Hamlin January KP-Healthy | 4.7 | 1.4 | 1.8 | 1.5 |
| Hamlin January KP-HLBs | 4.5 | 1.5 | 1.3 | 1.3 |
| Hamlin January WP-Healthy | 4.2 | 1.5 | 1.7 | 1.8 |
| Hamlin January WP-HLBa | 3.7 | 1.3 | 1.8 | 1.3 |
| Hamlin January WP-HLBs | 3.9 | 1.4 | 1.6 | 1.3 |
| Valencia April U-Healthy | 6.4 | 1.3 | 1.3 | 1.8 |
| Valencia April U-HLBa | 6.5 | 1.4 | 1.5 | 1.8 |
| Valencia April U-HLBs | 6.5 | 1.3 | 1.9 | 1.6 |
| Valencia April KP-Healthy | 7.0 | 1.8 | 1.5 | 2.6 |
| Valencia April KP-HLBa | 6.6 | 1.7 | 1.5 | 2.1 |
| Valencia April KP-HLBs | 6.0 | 3.0 | 2.3 | 3.1 |
| Valencia April MB-Healthy | 6.7 | 0.9 | 1.3 | 1.4 |
| Valencia April MB-HLBa | 6.0 | 1.3 | 1.5 | 2.0 |
| Valencia April MB-HLBs | 6.2 | 2.0 | 1.9 | 2.3 |

TABLE 9-continued

Table 9

| | | Mouthfeel descriptors | | |
|---|---|---|---|---|
| Sample | Body | Tingling | Astringent | Burning |
| Hamlin U-Healthy | 5.4 | 0.9 | 1.0 | 1.1 |
| Hamlin U-HLB | 5.1 | 1.5 | 2.0 | 1.5 |
| Hamlin KP-HLB Mild | 5.0 | 1.3 | 1.5 | 1.3 |
| Valencia Healthy | 6.2 | 1.2 | 1.6 | 1.9 |
| Valencia HLBa | 6.0 | 1.6 | 2.0 | 2.6 |
| Valencia HLBs | 5.8 | 2.4 | 2.5 | 2.9 |
| Hamlin WP-Healthy | 5.4 | 1.0 | 1.4 | 1.0 |
| Hamlin WP-HLB | 5.5 | 1.2 | 1.5 | 1.5 |
| Vaencia Blend 25% Healthy/75% HLB | 5.3 | 2.0 | 2.5 | 2.8 |
| Valencia Blend 75% Healthy/25% HLB | 5.7 | 1.8 | 2.2 | 2.6 |
| Valencia MB-Healthy | 6.0 | 1.5 | 2.0 | 2.3 |
| Valencia MB-HLB | 5.6 | 1.9 | 2.5 | 2.9 |
| Hamlin Blend 67% healthy/33% HLB | 4.6 | 1.4 | 1.7 | 1.5 |
| Hamlin KP-Healthy | 5.6 | 1.2 | 1.3 | 0.9 |
| Hamlin KP-HLB | 5.1 | 1.7 | 2.4 | 1.7 |
| HamlinKP-Healthy | 5.3 | 1.0 | 1.1 | 1.2 |
| Hamlin KP-HLB | 4.8 | 1.8 | 1.8 | 1.5 |
| Hamlin KP-HLB Severe | 4.6 | 1.8 | 2.0 | 1.7 |
| Hamlin U-Healthy | 5.5 | 1.0 | 1.2 | 1.1 |
| Hamlin U-HLB | 5.3 | 1.3 | 1.8 | 1.5 |
| Hamlin KP-HLB mild | 5.1 | 1.1 | 1.8 | 1.0 |
| Valencia Blend 50% Healthy/50% HLB | 5.7 | 2.5 | 2.7 | 3.2 |
| Valencia U-Healthy | 5.8 | 1.9 | 2.3 | 2.5 |
| Val U-HLB | 5.4 | 1.8 | 2.4 | 2.8 |
| Hamlin KP-HLB Severe | 5.1 | 1.7 | 2.2 | 1.7 |
| Hamlin WP-Healthy | 5.2 | 1.2 | 1.6 | 1.4 |
| Hamlin WP-HLB | 4.9 | 1.4 | 2.2 | 1.3 |

TABLE 10

Table 10

| | Aftertaste descriptors | | |
|---|---|---|---|
| Sample | Bitter | Astringent | Burning |
| Hamlin December Healthy | 1.8 | 1.7 | 1.9 |
| Hamlin Decmber HLBa | 5.2 | 2.8 | 2.7 |
| Hamlin December HLBs | 5.3 | 3.2 | 2.8 |
| Hamlin January Healthy | 1.1 | 1.2 | 1.0 |
| Hamlin January HLBa | 1.5 | 1.5 | 1.3 |
| Hamlin January HLBs | 2.8 | 2.3 | 2.1 |
| Valencia April Healthy | 1.6 | 1.4 | 2.5 |
| Valencia april HLBa | 1.6 | 1.4 | 2.0 |
| Valencia April HLBs | 1.9 | 1.8 | 2.5 |
| Hamlin April U-Healthy | 1.3 | 1.1 | 0.9 |
| Hamlin January U-HLBa | 2.3 | 1.7 | 1.4 |
| Hamlin January U-HBLs | 2.8 | 2.2 | 1.7 |
| Hamlin January KP-Healthy | 1.4 | 1.3 | 1.1 |
| Hamlin January KP-HLBs | 1.7 | 1.0 | 1.0 |
| Hamlin January WP-Healthy | 1.7 | 1.5 | 1.3 |
| Hamlin January WP-HLBa | 1.8 | 1.2 | 0.8 |
| Hamlin January WP-HLBs | 1.8 | 1.6 | 1.3 |
| Valencia April U-Healthy | 1.3 | 1.1 | 1.3 |
| Valencia April U-HLBa | 1.5 | 1.5 | 1.8 |
| Valencia April U-HLBs | 1.4 | 1.5 | 1.5 |
| Valencia April KP-Healthy | 1.6 | 1.5 | 1.8 |
| Valencia April KP-HLBa | 1.4 | 1.2 | 1.7 |
| Valencia April KP-HLBs | 2.0 | 1.8 | 2.2 |
| Valencia April MB-Healthy | 1.1 | 1.0 | 1.3 |
| Valencia April MB-HLBa | 1.5 | 1.2 | 1.5 |
| Valencia April MB-HLBs | 1.6 | 1.6 | 1.8 |
| Hamlin U-Healthy | 1.2 | 0.8 | 0.7 |
| Hamlin U-HLB | 2.1 | 1.4 | 1.1 |
| Hamlin KP-HLB Mild | 1.5 | 1.1 | 1.1 |
| Valencia Healthy | 1.0 | 1.1 | 1.2 |
| Valencia HLBa | 1.5 | 1.5 | 1.8 |
| Valencia HLBs | 1.7 | 1.7 | 1.9 |
| Hamlin WP-Healthy | 1.0 | 1.1 | 1.0 |
| Hamlin WP-HLB | 1.1 | 1.2 | 1.3 |
| Vaencia Blend 25% Healthy/75% HLB | 1.8 | 2.0 | 1.8 |
| Valencia Blend 75% Healthy/25% HLB | 1.7 | 2.0 | 2.0 |
| Valencia MB-Healthy | 1.4 | 1.6 | 1.8 |
| Valencia MB-HLB | 1.8 | 2.0 | 1.9 |
| Hamlin Blend 67% healthy/33% HLB | 1.8 | 1.3 | 1.0 |
| Hamlin KP-Healthy | 1.1 | 1.0 | 0.7 |
| Hamlin KP-HLB | 2.0 | 1.7 | 1.2 |
| HamlinKP-Healthy | 1.1 | 0.9 | 0.9 |
| Hamlin KP-HLB | 2.3 | 1.5 | 1.0 |
| Hamlin KP-HLB Severe | 2.0 | 1.2 | 1.3 |
| Hamlin U-Healthy | 1.3 | 1.3 | 1.3 |
| Hamlin U-HLB | 1.6 | 1.8 | 1.1 |
| Hamlin KP-HLB mild | 2.4 | 1.8 | 1.0 |
| Valencia Blend 50% Healthy/50% HLB | 1.9 | 2.0 | 2.2 |
| Valencia U-Healthy | 1.8 | 2.1 | 2.0 |
| Val U-HLB | 2.0 | 1.9 | 2.1 |
| Hamlin KP-HLB Severe | 2.3 | 2.1 | 1.5 |
| Hamlin WP-Healthy | 1.8 | 1.8 | 1.2 |
| Hamlin WP-HLB | 2.5 | 1.9 | 1.3 |

TABLE 11

Table 11

| Sample | Li Primer Ct value | LJ Primer Ct value |
|---|---|---|
| Hamlin December Healthy | 33.4 | 28.9 |
| Hamlin Decmber HLBa | 27.5 | 24.7 |
| Hamlin December HLBs | 27.0 | 24.1 |
| Hamlin January Healthy | 32.6 | 27.5 |
| Hamlin January HLBa | 30.7 | 26.9 |
| Hamlin January HLBs | 29.4 | 24.9 |
| Valencia April Healthy | 33.9 | 29.8 |
| Valencia April HLBa | 33.7 | 29.9 |
| Valencia April HLBs | 30.2 | 27.3 |
| Hamlin April U-Healthy | 34.6 | 28.3 |
| Hamlin January U-HLBa | 32.6 | 26.2 |
| Hamlin January U-HBLs | 31.2 | 25.1 |
| Hamlin January KP-Healthy | 32.8 | 29.1 |
| Hamlin January KP-HLBs | 32.1 | 28.5 |
| Hamlin January WP-Healthy | 31.2 | 27.2 |
| Hamlin January WP-HLBa | 30.8 | 26.4 |
| Hamlin January WP-HLBs | 29.3 | 25.6 |
| Valencia April U-Healthy | 35.7 | 32.9 |
| Valencia April U-HLBa | 32.9 | 30.5 |
| Valencia April U-HLBs | 32.7 | 29.6 |
| Valencia April KP-Healthy | 33.6 | 30.2 |
| Valencia April KP-HLBa | 33 | 29.8 |
| Valencia April KP-HLBs | 30.7 | 27.1 |
| Valencia April MB-Healthy | 35.8 | 31.2 |
| Valencia April MB-HLBa | 34.9 | 30.8 |
| Valencia April MB-HLBs | 32.3 | 28.7 |
| Hamlin U-Healthy | 40.0 | 33.4 |
| Hamlin U-HLB | 29.3 | 26.0 |
| Hamlin KP-HLB Mild | 30.4 | 26.5 |
| Valencia Healthy | 34.5 | 30.3 |
| Valencia HLBa | 31.2 | 29.3 |
| Valencia HLBs | 30.9 | 27.2 |
| Hamlin WP-Healthy | 40.0 | 30.5 |
| Hamlin WP-HLB | 33.8 | 27.8 |
| Vaencia Blend 25% Healthy/75% HLB | 33.2 | 29.5 |
| Valencia Blend 75% Healthy/25% HLB | 34.9 | 30.1 |
| Valencia MB-Healthy | 35.9 | 32.7 |
| Valencia MB-HLB | 32.3 | 27.5 |
| Hamlin Blend 67% healthy/33% HLB | 30.5 | 27.2 |
| Hamlin KP-Healthy | 36.3 | 31.5 |
| Hamlin KP-HLB | 29.2 | 25.0 |
| HamlinKP-Healthy | 36.1 | 30.4 |
| Hamlin KP-HLB | 30.2 | 26.4 |

TABLE 11-continued

Table 11

| Sample | Li Primer Ct value | LJ Primer Ct value |
|---|---|---|
| Hamlin KP-HLB Severe | 29.1 | 26.0 |
| Hamlin U-Healthy | 40.0 | 32.3 |
| Hamlin U-HLB | 30.4 | 27.0 |
| Hamlin KP-HLB mild | 30.0 | 25.1 |
| Valencia Blend 50% Healthy/50% HLB | 34.9 | 30.5 |
| Valencia U-Healthy | 35.7 | 31.6 |
| Valencia U-HLB | 32.4 | 28.4 |
| Hamlin KP-HLB Severe | 29.7 | 25.0 |
| Hamlin WP-Healthy | 33.2 | 30.9 |
| Hamlin WP-HLB | 31.1 | 25.5 |

Figure 2A:
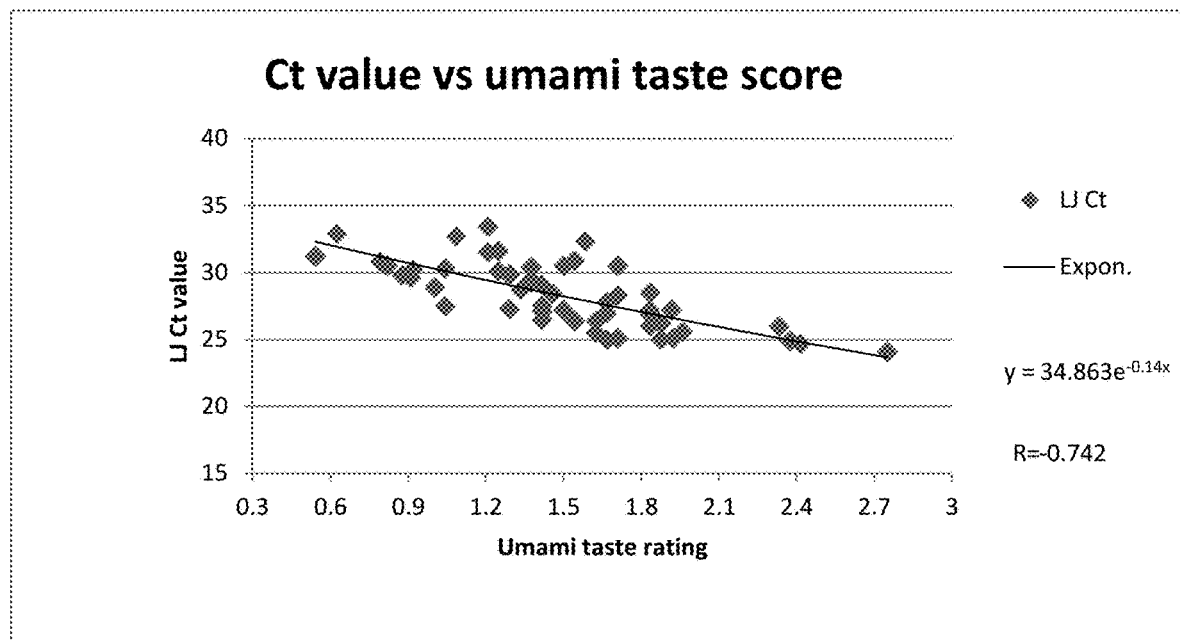
FIG. 2A illustrates the Ct value vs. umami taste score.
Figure 2B:
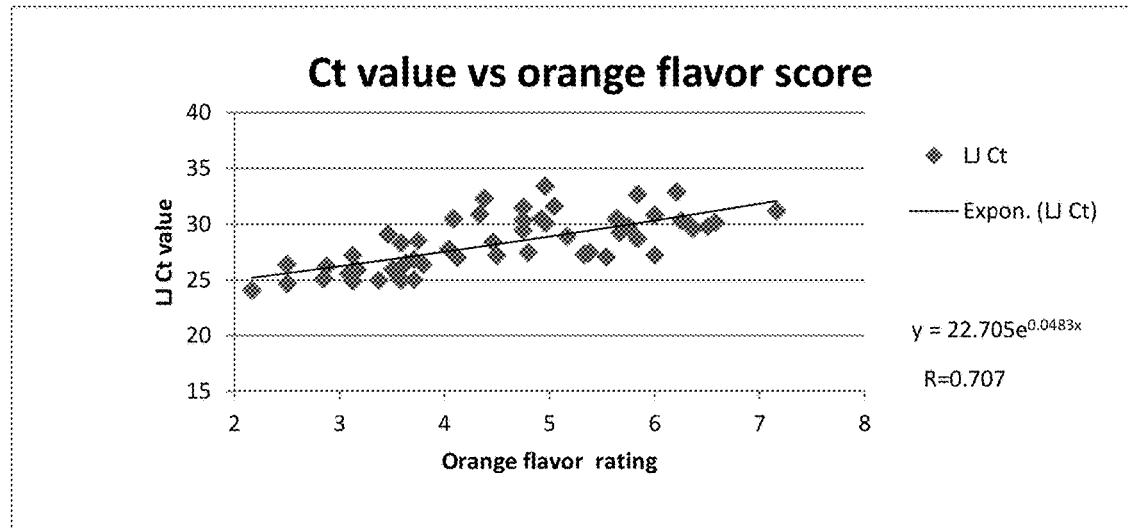
FIG. 2B illustrates the Ct value vs. orange flavor score.
Figure 2C:
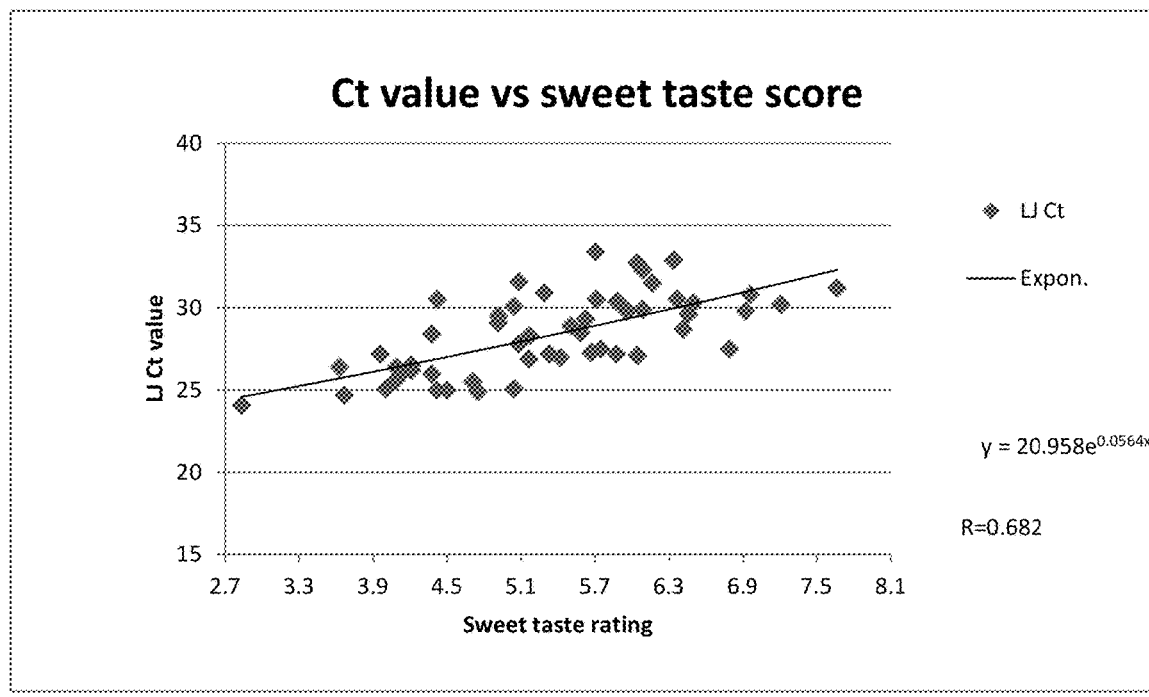
FIG. 2C illustrates the Ct value vs. sweet taste score.
Figure 3A:
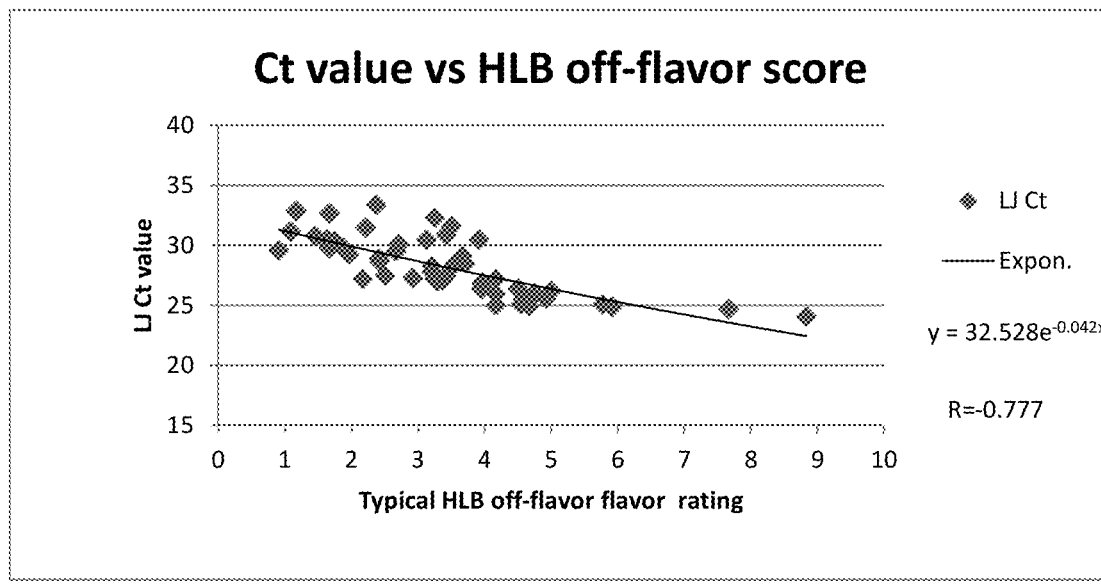
FIG. 3A illustrates the Ct value vs. HLB off-flavor score.
Figure 3B:
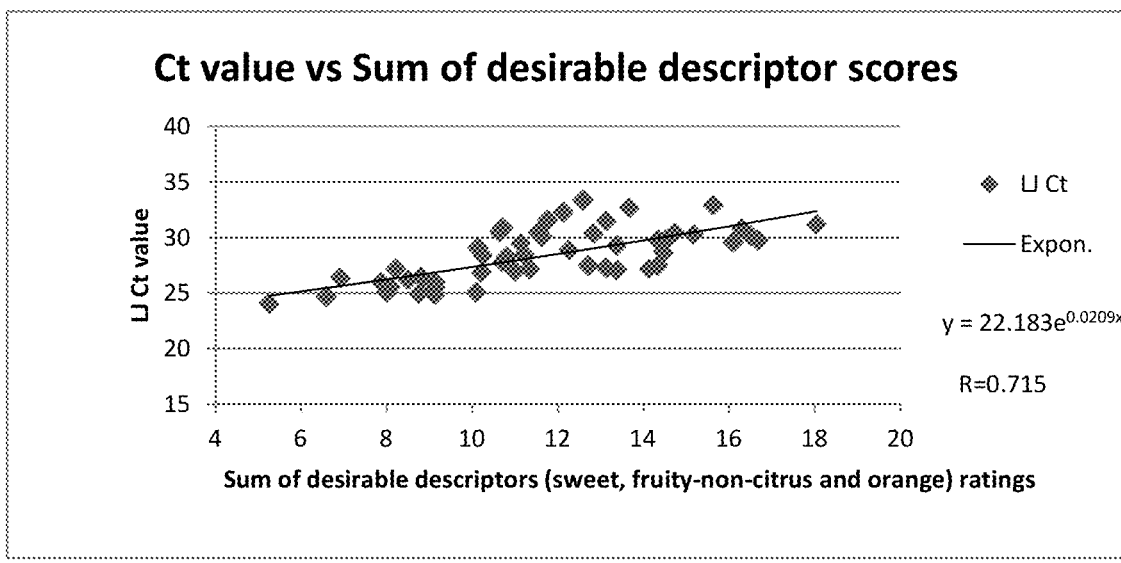
FIG. 3B illustrates the Ct value vs. the sum of desirable descriptor scores.
Figure 3C:
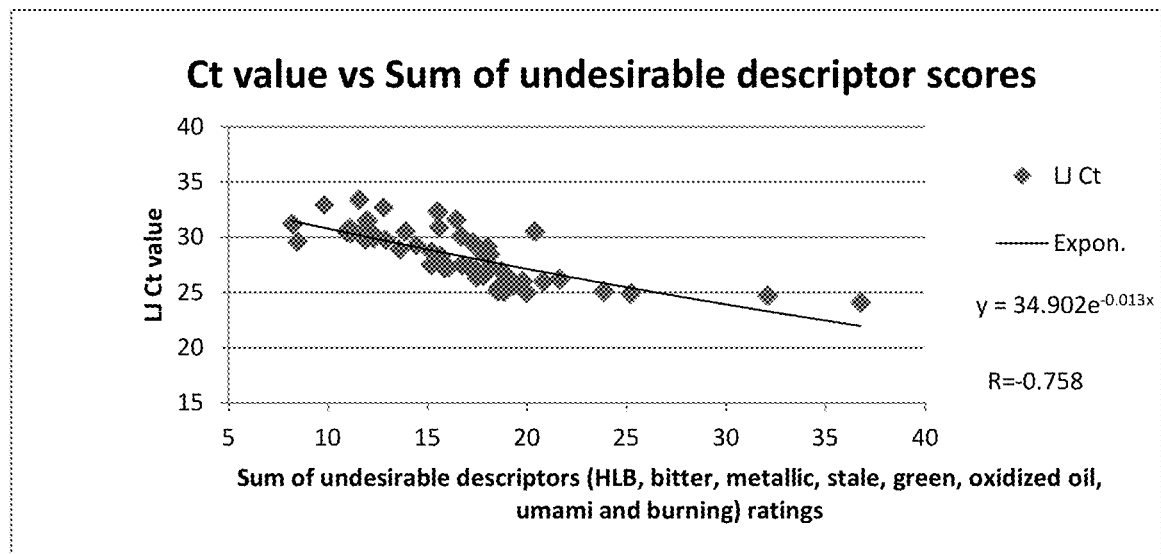
FIG. 3C illustrates the Ct value vs. the sum of undesirable descriptor scores.

In Table 11, the higher the Ct value, the less CLas DNA in the juice sample, and the lower the Ct value, the higher the CLas DNA in the juice sample. However, because the relative Ct values and the abundance of the target DNA (in this example, the CLas titer/load in orange juice) is an exponential relationship, an exponential (logistic) regression is used to fit Ct values to sensory descriptor ratings because an exponential regression shows slightly better curve fit than linear (see FIGS. 2A, 2B, 2C and 3A, 3B, 3C). The LJ primers give a slightly better regression fit to the sensory data than did the Li primers, so correlations to the sensory descriptors ("umami", "orange", and "sweet") scores are shown for the LJ primer with R=(−) 0.74 for Ct value versus "umami" taste score (FIG. 2A), R=(+) 0.70 for Ct value vs. "orange" flavor score (FIG. 2B), and R=(+) 0.68 for Ct value vs. "sweet" taste score (FIG. 2C). Correlations to the sensory descriptors ("typical HLB off-flavor", combination of desirable orange juice descriptors, and combined undesirable descriptors) scores are shown for the LJ primer with R=(−) 0.78 for Ct value vs. "typical HLB off-flavor" score (FIG. 3A), R=(+) 0.71 for combined ratings for desirable orange juice descriptors score that had significant correlations individually (sweet, fruity-noncitrus, and orange) (FIG. 3B), and R=(−) 0.76 for combined undesirable descriptors for orange juice flavor score that had significant correlations individually (HLB, bitter, metallic, stale, green, oxidized oil, umami and burning) (FIG. 3C). These correlations show that higher Ct values, indicating less CLas DNA in the juice, correlates with desirable orange juice flavor descriptors, and lower Ct values, indicating more CLas DNA in the juice, correlate positively with undesirable orange juice flavor descriptors including typical HLB off-flavor, and therefore, could be used to predict flavor quality of orange juice.

Thus, one can use qPCR and the indicated primers to determine the amount of off-flavor in the orange juice caused by CLas. With this knowledge orange juice processors will be able to make informed decisions as to grading and blending the incoming juice based on the quality indication of how much CLas DNA is in the juice. Having a quick, routine and objective measure, such as CLas Ct value, would be much cheaper and less time consuming than running a sensory panel on each truckload of fruit juice. Running sensory panels (also called tasting panels) requires constantly training of panelists, who must be paid, and then suffering inconsistent panel ratings because of illness (such as colds that interfere with tasting ability), fatigue, personal distractions, etc. Humans on sensory panel cannot be completely objective as each person's tasting abilities are not consistent.

Example 5 Quality Control Assay to Identify Microorganism in Juice/Cider

Figure 4:
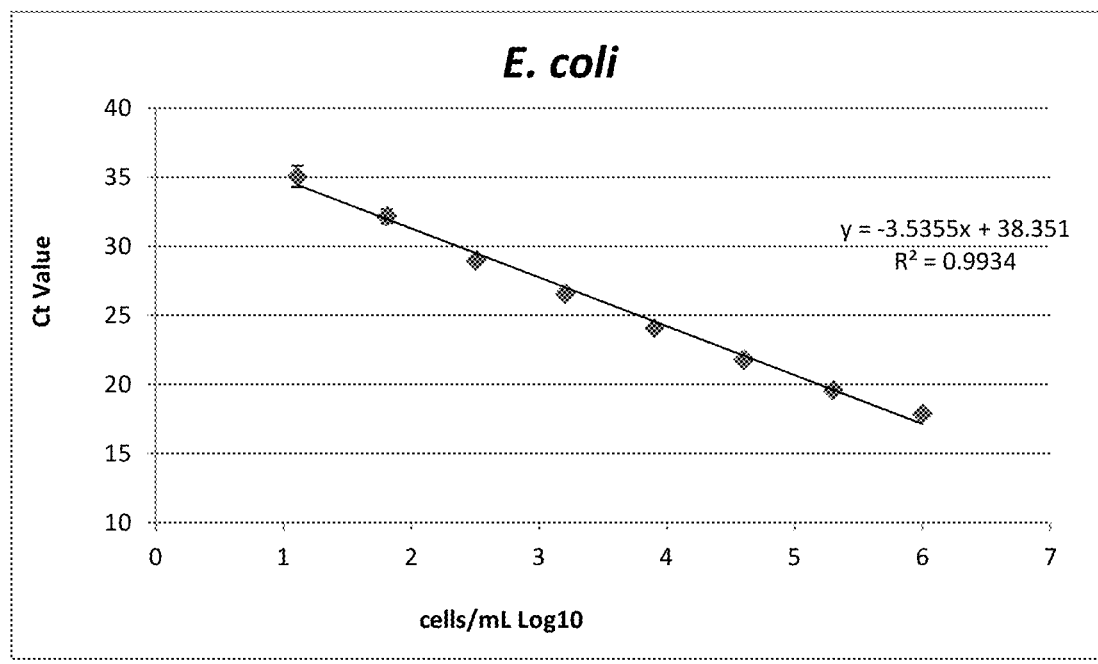
FIG. 4 illustrates the Ct value of *E. coli* amplified DNA in orange juice vs. the number of *E. coli* cells per ml of juice (in $\log_{10}$).
Figure 5:
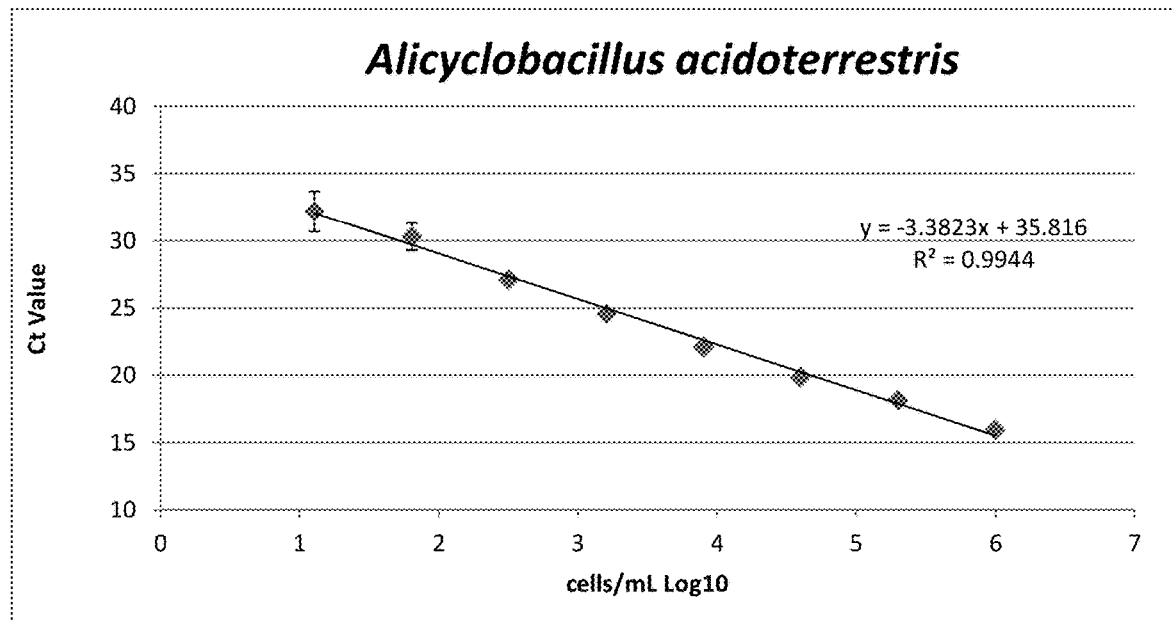
FIG. 5 illustrates the Ct value of *Alicyclobacillus acidoterrestris* amplified DNA in orange juice vs. the number of *A. acidoterrestris* cells per ml of juice (in $\log_{10}$).
Figure 6:
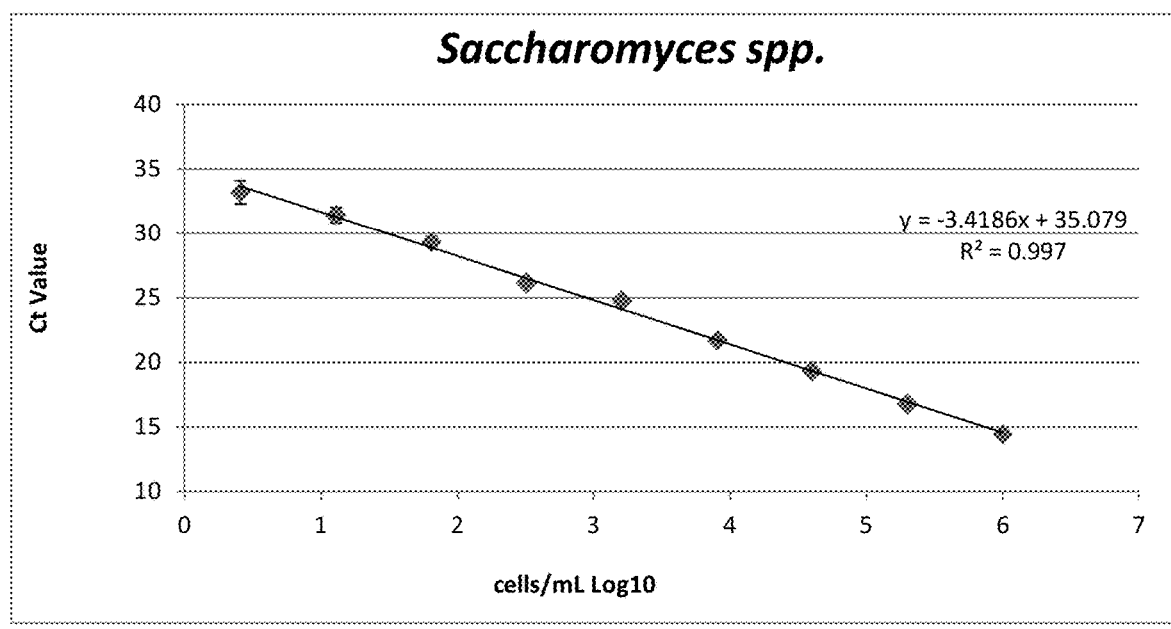
FIG. 6 illustrates the Ct value of *Saccharomyces* spp. amplified DNA in orange juice vs. the number of *Saccharomyces* spp. cells per ml of juice (in $\log_{10}$).
Figure 7:
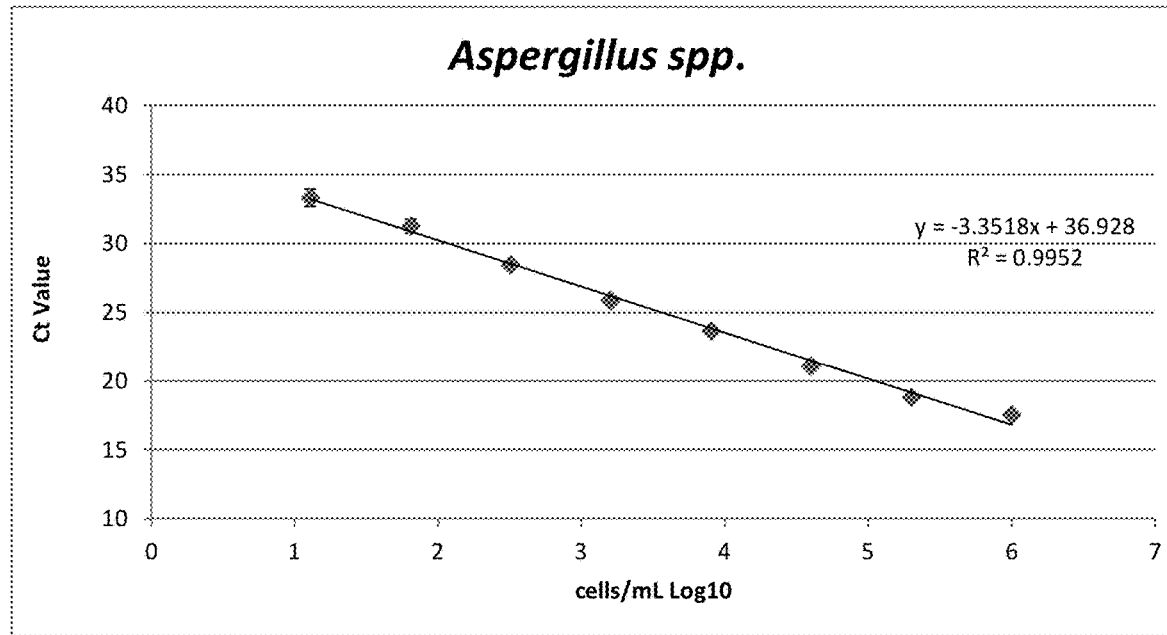
FIG. 7 illustrates the Ct value of *Aspergillus* spp. amplified DNA in orange juice vs. the number of *Aspergillus* spp. cells per ml of juice (in $\log_{10}$).

Individual samples of orange juice (healthy) are separately inoculated with *Alicyclobacillus acidoterrestris*, *Saccharomyces* spp., *Aspergillus* spp., and *E. coli* to the concentration of 1×10$^6$ CFU/ml. The inoculated juice samples are then 5 fold serially diluted into new orange juice until the most diluted juice sample reaches the concentration of 2.56 CFU/ml. Isolation of nucleic acids from the juice occurs using the methods described in Example 1, supra. qPCR parameters are used as described in Example 2, supra, but using the primers in Table 12, infra, for the indicated microorganism at 250 nM. Standard curves for each inoculated microorganism are generated based on the concentrations of microorganism and their corresponding Ct values generated by qPCR analysis (see FIGS. 4 (*E. coli*), 5 (*A. acidoterrestris*), 6 (*Saccharomyces* spp.), and 7 (*Aspergillus* spp.)). For *E. coli*, a Ct value of approximately 35 or less when using SEQ ID NOs: 12 and 13 as primers indicates the presence of *E. coli* in a juice or cider. For *A. acidoterrestris*, a Ct value of approximately 33 or less when using SEQ ID NOs: 6 and 7 as primers indicates the presence of *A. acidoterrestris* in a juice or cider. For *Saccharomyces* spp., a Ct value of approximately 34 or less when using SEQ ID NOs: 8 and 9 as primers indicates the presence of *Saccharomyces* spp. in a juice or cider. For *Aspergillus* spp., a Ct value of approximately 34 or less when using SEQ ID NOs: 10 and 11 indicates presence of *Aspergillus* spp. in a juice or cider. These Ct values can serve has the reference.

To detect these microorganisms in orange juice, a sample of orange juice is processed using the methods described in Example 1 to isolate the nucleic acids in the juice. Then the isolated nucleic acids are processed using the qPCR methods set forth in Example 2 to amplify DNA using the primers in Table 12 for the indicated microorganism. The concentration of each primer is 250 nM for the qPCR reaction. Upon obtaining the Ct value for a particular microorganism, that value is compared to the known standards to determine if the particular microorganism is present in the juice. A sample of the juice is also added to medium suitable for growing the particular microorganism and incubated at their suitable growing temperatures. The culture is also tested for the presence of the particular microorganism to confirm the results of the qPCR. For each microorganism tested, the results from qPCR and the confirmatory incubation matched.

TABLE 12

| Microorganism | Primers | Target | Source |
|---|---|---|---|
| *Alicyclobacillus acidoterrestris* | forward: ATGCAGAGTTCGAACG (SEQ ID NO: 6)<br>reverse: AAGCTGCCGAAGCACTC (SEQ ID NO: 7) | squalenehopene cyclase (SHC) encoding gene, shc | 1 |
| *Saccharomyces* spp. | forward: GAAAACTCCACAGTGTGTTG (SEQ ID NO: 8)<br>reverse: GCTTAAGTGCGCGGTCTTG (SEQ ID NO: 9) | internal transcribed spacers ITS (rDNA) | 2 |

TABLE 12-continued

| Microorganism | Primers | Target | Source |
|---|---|---|---|
| Aspergillus spp. | forward: CTTGGATTTGCTGAAGACTAAC (SEQ I D NO: 10) reverse: CTAACTTTCGTTCCCTGATTAATG (SEQ ID NO: 11) | 18S rRNA gene | 3 |
| E. coli | forward: ATGGAATTTCGCCGATTTTGC (SEQ ID NO:12) reverse: ATTGTTTGCCTCCCTGCTGC (SEQ ID NO: 13) | uidA | 4 |

1. Luo, et al., Letters in Applied Microbiology 39:376-382 (2004)
2. Zott, et al., Food Microbiol. 27(5):559-567 (2010)
3. Gemma, et al., PLoS One 7(7): e40022 (2012)
4. Heijnen and Medema, J. Water Health 4:487-98 (2006)

Figure 8:
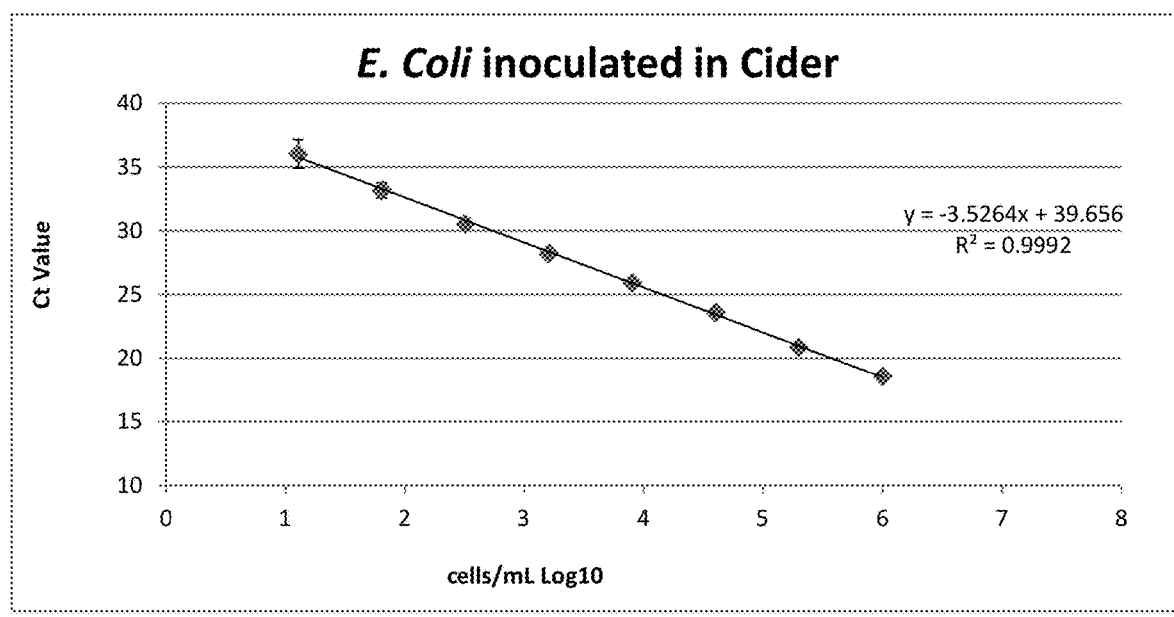
FIG. 8 illustrates the Ct value of *E. coli* amplified DNA in apple cider vs. the number of *E. coli* cells per ml of juice (in $\log_{10}$).

To assay for presence of *E. coli* in apple cider, Zeigler's Old-Fashioned Apple Cider® is purchased from a local store. *E. coli* is added to the cider to a concentration of $1 \times 10^6$ CFU/ml. Next, the inoculated apple cider is serially diluted five fold into new apple cider until the most diluted cider sample contain 2.56 CFU/ml *E. coli*. DNA is extracted from the inoculated cider using the DNA extraction method described supra in Example 1. Next, qPCR is performed using 250 mM each of forward primer (SEQ ID NO: 12) and reverse primer (SEQ ID NO: 13) with the other reaction parameters as described supra in Example 2. A standard curve is generated based on the concentrations of *E. coli* and the corresponding Ct values generated by qPCR analysis (see FIG. 8).

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation. All documents cited herein are incorporated by reference. All numeric values provided herein include a 10% increase and a 10% decrease of that value. So, "ten" includes all numbers between "nine" and "eleven"; "one hundred" includes all numbers between "ninety" and "one hundred ten". All documents cited herein are incorporated by reference.

The invention claimed is:

1. A method for isolating nucleic acids from a pectin containing juice or cider comprising:
   (a) separating solid components from liquid components of said pectin containing juice or cider;
   (b) lysing cells present in said solid components to release nucleic acids, proteins, polysaccharides, lipids, and non-polar material present in said cells;
   (c) generating an organic phase, an interface, and an aqueous phase wherein said lipids are in said organic phase; wherein said proteins are in said interface; and wherein said nucleic acids and polysaccharides are in said aqueous phase;
   (d) separating said aqueous phase from said organic phase and said interface;
   (e) mixing an aqueous solution of cetyl trimethyl ammonium bromide (CTAB) and salt with said polysaccharides and nucleic acids, wherein said nucleic acids precipitate out of said aqueous solution, and wherein said polysaccharides remain dissolved in said aqueous solution; and
   (f) separating said aqueous solution containing said dissolved polysaccharides from said nucleic acids.

2. The method of claim 1 wherein said concentration of said salt in said aqueous solution is between approximately 10 mM and approximately 400 mM.

3. A method for isolating nucleic acids from a pectin containing juice or cider comprising:
   (a) separating solid components present in a sample of liquid components of said pectin containing juice or cider;
   (b) exposing said solid components to a solution containing Tris-base, EDTA, salt, PVP40, β-mercaptoethanol, NaOH, and a surfactant to dissolve said solid components and lyse cells present in said solid material;
   (c) optionally heating said solution to lyse said cells;
   (d) adding chloroform to generate an aqueous phase, an interphase, and an organic phase, wherein lipids and non-polar material are in said organic phase, wherein nucleic acids and polysaccharides are in said aqueous phase, and wherein proteins are in said interface;
   (e) separating said aqueous phase from said organic phase and said interface;
   (f) adding CTAB to said aqueous phase, wherein said nucleic acids present in said aqueous phase precipitate out of said aqueous phase;
   (g) optionally heating said aqueous phase and CTAB to enhance precipitation of said nucleic acids;
   (h) separating said nucleic acids from said aqueous phase;
   (i) optionally washing said nucleic acids in ethanol to remove any remaining CTAB; and
   (j) optionally separating said washed nucleic acids from said ethanol.

4. A method for determining if a pectin containing juice or cider that is potentially contaminated with a microorganism is safe for consumption by an animal, said method comprising:
   (a) isolating nucleic acids from said pectin containing juice or cider using the method of claim 1;
   (b) quantifying the amount of said nucleic acids belonging to said microorganism in said pectin containing juice or cider; and
   (c) comparing amount of said nucleic acids belonging to said microorganism in said pectin containing juice or cider to a known value that indicates maximum quantity of said microorganism that is safe for consumption by said animal.

5. The method of claim 4, wherein said quantifying step further comprises
   (i) exposing said isolated nucleic acids to a first primer, a second primer, and a label, wherein said first primer's sequence and said second primer's sequence are complementary to specific sequences in said microorganism's genome and bind to said specific sequences in said microorganism's genome;
   (ii) amplifying said microorganism's nucleic acids to generate an amplicon; and
   (iii) determining Ct value of said amplified nucleic acids.

6. The method of claim 5, wherein said label is selected from the group consisting of an intercalating dye, a fluorescent composition, a spectroscopic label, a photochemical label, a biochemical label, an immunochemical label, and a chemical label.

7. The method of claim 4, wherein said microorganism is selected from the group consisting of lactic acid bacteria, acetic acid bacteria, *Alicyclobacillus* spp., *Zygosaccharomyces* spp., *Rhodotorula* ruba, *Escherichia coli*, *Listeria* spp., *Shigella* spp., *Salmonella* spp., and *Klebsiella* spp., *Saccharomyces* spp., *Aspergillus* spp.

* * * * *